US008864809B2

(12) United States Patent
Miles et al.

(10) Patent No.: US 8,864,809 B2
(45) Date of Patent: Oct. 21, 2014

(54) SYSTEMS AND DEVICES FOR REDUCING THE SIZE OF AN INTERNAL TISSUE OPENING

(75) Inventors: Scott D. Miles, Sandy, UT (US); Clark C. Davis, Holladay, UT (US); DeWayne C. Fox, South Jordan, UT (US); Daryl R. Edmiston, Draper, UT (US); Richard J. Linder, Sandy, UT (US)

(73) Assignee: Coherex Medical, Inc., Salt Lake City, UT (US)

( * ) Notice: Subject to any disclaimer, the term of this patent is extended or adjusted under 35 U.S.C. 154(b) by 577 days.

(21) Appl. No.: 11/836,013

(22) Filed: Aug. 8, 2007

(65) Prior Publication Data
US 2008/0039922 A1  Feb. 14, 2008

Related U.S. Application Data

(60) Provisional application No. 60/821,947, filed on Aug. 9, 2006, provisional application No. 60/821,949, filed on Aug. 9, 2006, provisional application No. 60/829,507, filed on Oct. 13, 2006, provisional application No. 60/866,047, filed on Nov. 15, 2006, provisional application No. 60/942,625, filed on Jun. 7, 2007.

(51) Int. Cl.
*A61F 2/84* (2006.01)
*A61B 17/12* (2006.01)
*A61B 17/00* (2006.01)

(52) U.S. Cl.
CPC ... *A61B 17/0057* (2013.01); *A61B 2017/00867* (2013.01); *A61B 2017/00858* (2013.01);
(Continued)

(58) Field of Classification Search
USPC ............... 606/213, 139, 144, 148, 151, 108, 606/191–200; 623/1.11–1.25, 2.11
See application file for complete search history.

(56) References Cited

U.S. PATENT DOCUMENTS 2,755,060 A  7/1956 Twyman
3,874,388 A  4/1975 King et al.
(Continued)

FOREIGN PATENT DOCUMENTS

EP  0539125 B1  4/1993
EP  0541063 B1  9/1998
(Continued)

OTHER PUBLICATIONS

"Intravascular Occluding Device using a Modified Gianturco Stent as a Coil Cage." Wilson, Godon, LaBerge, Saavedra and Kerlan. JVIR. 2000.
(Continued)

*Primary Examiner* — Mark Mashack
(74) *Attorney, Agent, or Firm* — Holland and Hart LLP

(57) ABSTRACT

A medical system for treating an internal tissue opening can include a closure device and associated delivery device. The closure device can include a multi-cellular body portion operatively associated with a first anchor and a second anchor. The closure device can be configured to apply lateral force to tissue of the internal tissue opening for tissue approximation. The closure device can also include an ingrowth material. The delivery device can include an actuating assembly configured to partially deploy the closure device by a first movement, and deploy a second portion of the closure device by a second movement. The delivery device can also include a release assembly to selectively release or disconnect the closure device from the delivery device.

15 Claims, 12 Drawing Sheets

(52) U.S. Cl.
CPC . *A61B 17/12172* (2013.01); *A61B 2017/00407* (2013.01); *A61B 2017/00654* (2013.01); *A61B 2017/00619* (2013.01); *A61B 2017/00884* (2013.01); *A61B 2017/00084* (2013.01); *A61B 17/12168* (2013.01); *A61B 2017/00588* (2013.01); *A61B 2017/00575* (2013.01); *A61B 2017/00592* (2013.01); *A61B 2017/0061* (2013.01); *A61B 2017/00623* (2013.01); *A61B 2017/00862* (2013.01); *A61B 2017/00606* (2013.01); *A61B 17/12122* (2013.01); *A61B 2017/00597* (2013.01); *A61B 2017/12054* (2013.01); *A61B 2017/00601* (2013.01); *A61B 2017/00579* (2013.01)
USPC .......................................... 623/1.11; 606/139

(56) References Cited

U.S. PATENT DOCUMENTS

| | | |
|---|---|---|
| 4,007,743 A | 2/1977 | Blake |
| 4,708,140 A | 11/1987 | Baron |
| 4,762,129 A | 8/1988 | Bonzel |
| 4,840,185 A | 6/1989 | Hernandez |
| 4,917,089 A | 4/1990 | Sideris |
| 4,957,501 A | 9/1990 | Lahille et al. |
| 4,988,356 A | 1/1991 | Crittendon et al. |
| 5,002,531 A | 3/1991 | Bonzel |
| 5,040,548 A | 8/1991 | Yock |
| 5,041,093 A | 8/1991 | Chu |
| 5,108,420 A | 4/1992 | Marks |
| 5,171,259 A | 12/1992 | Inoue |
| 5,217,450 A | 6/1993 | Prior et al. |
| 5,232,445 A | 8/1993 | Bonzel |
| 5,234,458 A | 8/1993 | Metais |
| 5,300,085 A | 4/1994 | Yock |
| 5,334,217 A | 8/1994 | Das |
| 5,339,803 A | 8/1994 | Mayzels et al. |
| 5,425,744 A | 6/1995 | Fagan et al. |
| 5,433,723 A * | 7/1995 | Lindenberg et al. ........... 606/198 |
| 5,451,235 A | 9/1995 | Lock et al. |
| 5,484,449 A | 1/1996 | Amundson et al. |
| 5,496,277 A | 3/1996 | Termin et al. |
| 5,501,227 A | 3/1996 | Yock |
| 5,578,045 A | 11/1996 | Das |
| 5,634,931 A | 6/1997 | Kugel |
| 5,643,317 A | 7/1997 | Pavcnik et al. |
| 5,683,411 A | 11/1997 | Kavteladze et al. |
| 5,702,421 A | 12/1997 | Schneidt |
| 5,709,224 A | 1/1998 | Behl et al. |
| 5,725,552 A | 3/1998 | Kotula et al. |
| 5,766,184 A | 6/1998 | Matsuno et al. |
| 5,776,142 A * | 7/1998 | Gunderson ................... 623/1.11 |
| 5,846,261 A | 12/1998 | Kotula et al. |
| 5,853,422 A * | 12/1998 | Huebsch et al. ............... 606/213 |
| 5,861,003 A | 1/1999 | Latson et al. |
| 5,879,366 A | 3/1999 | Shaw et al. |
| 5,904,703 A | 5/1999 | Gilson |
| 5,916,145 A | 6/1999 | Chu et al. |
| 5,944,738 A | 8/1999 | Amplatz et al. |
| 5,993,484 A | 11/1999 | Shmulewitz |
| 6,004,328 A | 12/1999 | Solar |
| 6,007,563 A | 12/1999 | Nash et al. |
| 6,077,281 A | 6/2000 | Das |
| 6,077,291 A | 6/2000 | Das |
| 6,080,182 A * | 6/2000 | Shaw et al. .................... 606/213 |
| 6,165,167 A | 12/2000 | Delaloye |
| 6,168,616 B1 | 1/2001 | Brown, III |
| 6,174,322 B1 | 1/2001 | Schneidt |
| 6,196,995 B1 | 3/2001 | Fagan |
| 6,200,336 B1 | 3/2001 | Pavcnik et al. |
| 6,206,907 B1 | 3/2001 | Marino et al. |
| 6,210,338 B1 | 4/2001 | Afremov et al. |
| 6,214,029 B1 | 4/2001 | Thill et al. |
| 6,241,678 B1 | 6/2001 | Afremov et al. |
| 6,267,777 B1 | 7/2001 | Bosma et al. |
| 6,273,901 B1 | 8/2001 | Whitcher et al. |
| 6,355,052 B1 | 3/2002 | Neuss et al. |
| 6,368,339 B1 | 4/2002 | Amplatz |
| 6,375,671 B1 | 4/2002 | Kobayashi et al. |
| 6,379,368 B1 | 4/2002 | Corcoran et al. |
| 6,395,017 B1 * | 5/2002 | Dwyer et al. .................. 623/1.11 |
| 6,482,221 B1 | 11/2002 | Hebert et al. |
| 6,551,344 B2 | 4/2003 | Thill |
| 6,589,207 B1 | 7/2003 | El-Nounou |
| 6,592,549 B2 | 7/2003 | Gerdts et al. |
| 6,596,013 B2 | 7/2003 | Yang et al. |
| 6,605,062 B1 | 8/2003 | Hurley et al. |
| 6,605,109 B2 | 8/2003 | Fiedler |
| 6,613,075 B1 | 9/2003 | Healy et al. |
| 6,645,225 B1 | 11/2003 | Atkinson et al. |
| 6,645,239 B1 | 11/2003 | Park et al. |
| 6,679,909 B2 | 1/2004 | McIntosh et al. |
| 6,689,144 B2 | 2/2004 | Gerberding |
| 6,709,667 B1 | 3/2004 | Lowe et al. |
| 6,712,836 B1 | 3/2004 | Berg et al. |
| 6,723,071 B2 | 4/2004 | Gerdts et al. |
| 6,743,210 B2 * | 6/2004 | Hart et al. ....................... 604/194 |
| 6,793,667 B2 | 9/2004 | Hebert et al. |
| 6,800,065 B2 | 10/2004 | Duane et al. |
| 6,893,417 B2 | 5/2005 | Gribbons et al. |
| 6,932,832 B2 | 8/2005 | Patel et al. |
| 6,939,352 B2 * | 9/2005 | Buzzard et al. ................ 606/108 |
| 6,979,311 B2 | 12/2005 | Miles et al. |
| 6,979,991 B2 | 12/2005 | Burns et al. |
| 6,994,689 B1 | 2/2006 | Zadno-Azizi et al. |
| 7,037,293 B2 | 5/2006 | Carrillo et al. |
| 7,087,088 B2 | 8/2006 | Berg et al. |
| 7,122,043 B2 | 10/2006 | Greenhalgh et al. |
| 7,137,990 B2 | 11/2006 | Hebert et al. |
| 7,169,165 B2 | 1/2007 | Belef et al. |
| 7,179,252 B2 | 2/2007 | Agro et al. |
| 7,708,755 B2 | 5/2010 | Davis, III et al. |
| 8,062,325 B2 | 11/2011 | Mitelberg et al. |
| 2001/0007939 A1 | 7/2001 | Fleischman |
| 2001/0037129 A1 * | 11/2001 | Thill ............................. 606/213 |
| 2001/0039434 A1 | 11/2001 | Frazier et al. |
| 2002/0095141 A1 | 7/2002 | Belef et al. |
| 2002/0100485 A1 * | 8/2002 | Stevens et al. ................ 128/898 |
| 2002/0169475 A1 | 11/2002 | Gainor et al. |
| 2003/0028213 A1 * | 2/2003 | Thill et al. .................... 606/200 |
| 2003/0028235 A1 | 2/2003 | McIntosh et al. |
| 2003/0109886 A1 | 6/2003 | Keegan et al. |
| 2003/0139819 A1 | 7/2003 | Beer et al. |
| 2003/0167060 A1 * | 9/2003 | Buzzard et al. ................ 606/108 |
| 2003/0181942 A1 | 9/2003 | Sutton et al. |
| 2003/0191479 A1 | 10/2003 | Thornton et al. |
| 2003/0191495 A1 | 10/2003 | Ryan et al. |
| 2003/0195561 A1 | 10/2003 | Carley et al. |
| 2003/0199987 A1 | 10/2003 | Berg et al. |
| 2003/0208232 A1 | 11/2003 | Blaeser et al. |
| 2003/0225421 A1 | 12/2003 | Peavey et al. |
| 2004/0010285 A1 | 1/2004 | Carley et al. |
| 2004/0044361 A1 | 3/2004 | Frazier et al. |
| 2004/0073242 A1 | 4/2004 | Chandusko |
| 2004/0073252 A1 | 4/2004 | Goldberg et al. |
| 2004/0098042 A1 | 5/2004 | Devellian et al. |
| 2004/0111095 A1 * | 6/2004 | Gordon et al. ................. 606/108 |
| 2004/0133236 A1 | 7/2004 | Chandusko |
| 2004/0143294 A1 | 7/2004 | Corcoran et al. |
| 2004/0176799 A1 | 9/2004 | Chanduszko et al. |
| 2004/0220596 A1 | 11/2004 | Frazier et al. |
| 2004/0220610 A1 | 11/2004 | Kreidler et al. |
| 2004/0220612 A1 | 11/2004 | Swainston et al. |
| 2004/0254594 A1 | 12/2004 | Alfaro |
| 2004/0267306 A1 | 12/2004 | Blaeser et al. |
| 2005/0027305 A1 * | 2/2005 | Shiu et al. ..................... 606/108 |
| 2005/0033327 A1 | 2/2005 | Gainor et al. |
| 2005/0034735 A1 | 2/2005 | Deem et al. |
| 2005/0049681 A1 * | 3/2005 | Greenhalgh et al. .......... 623/1.15 |
| 2005/0055050 A1 | 3/2005 | Alfaro |
| 2005/0065547 A1 | 3/2005 | Marino et al. |
| 2005/0075656 A1 * | 4/2005 | Beaupre ......................... 606/153 |
| 2005/0080476 A1 * | 4/2005 | Gunderson et al. ........... 623/1.11 |
| 2005/0113902 A1 | 5/2005 | Geiser et al. |

(56) References Cited

U.S. PATENT DOCUMENTS

| | | |
|---|---|---|
| 2005/0125032 A1 | 6/2005 | Whisenant et al. |
| 2005/0222603 A1 | 10/2005 | Andreas et al. |
| 2005/0228434 A1 | 10/2005 | Amplatz et al. |
| 2005/0228475 A1* | 10/2005 | Keeble et al. ............... 623/1.11 |
| 2005/0234509 A1 | 10/2005 | Widomski et al. |
| 2005/0251154 A1 | 11/2005 | Chanduszko et al. |
| 2005/0251201 A1 | 11/2005 | Roue et al. |
| 2005/0256532 A1 | 11/2005 | Nayak et al. |
| 2005/0267524 A1 | 12/2005 | Chanduszko |
| 2005/0267525 A1 | 12/2005 | Chanduszko |
| 2005/0288706 A1 | 12/2005 | Widomski et al. |
| 2005/0288786 A1 | 12/2005 | Chanduszko |
| 2006/0009799 A1 | 1/2006 | Kleshinski et al. |
| 2006/0106420 A1 | 5/2006 | Dolan et al. |
| 2006/0116710 A1 | 6/2006 | Corcoran |
| 2006/0122647 A1 | 6/2006 | Callaghan et al. |
| 2006/0178694 A1 | 8/2006 | Greenhalgh et al. |
| 2006/0271089 A1 | 11/2006 | Alejandro et al. |
| 2007/0073389 A1 | 3/2007 | Bolduc et al. |
| 2007/0100356 A1 | 5/2007 | Lucatero et al. |
| 2007/0255390 A1* | 11/2007 | Ducke et al. ............... 623/1.11 |
| 2007/0270905 A1* | 11/2007 | Osborne ............... 606/213 |
| 2008/0015636 A1 | 1/2008 | Olsen et al. |
| 2009/0030495 A1* | 1/2009 | Koch ............... 623/1.11 |

FOREIGN PATENT DOCUMENTS

| | | |
|---|---|---|
| EP | 0545091 B1 | 7/1999 |
| EP | 0614342 B1 | 7/1999 |
| EP | 1013227 B1 | 6/2000 |
| EP | 1046375 B1 | 10/2000 |
| EP | 0474752 B2 | 12/2000 |
| EP | 0861049 B1 | 4/2001 |
| EP | 0698373 B1 | 11/2003 |
| EP | 1179999 B1 | 1/2006 |
| EP | 1211983 B1 | 3/2007 |
| EP | 1864613 A1 | 12/2007 |
| EP | 1222897 B1 | 3/2008 |
| EP | 1923005 A2 | 5/2008 |
| EP | 1923019 A1 | 5/2008 |
| WO | WO0149185 A1 | 7/2001 |
| WO | WO 03/068302 * | 8/2003 |
| WO | WO03082076 A2 | 10/2003 |
| WO | WO2004052213 A1 | 6/2004 |
| WO | WO2004091411 A2 | 10/2004 |
| WO | WO2004103162 A2 | 12/2004 |
| WO | WO2004103209 | 12/2004 |
| WO | WO2005034738 A2 | 4/2005 |
| WO | WO2006028813 A2 | 3/2006 |
| WO | WO2006036837 A2 | 4/2006 |
| WO | WO2006062711 A2 | 6/2006 |
| WO | WO2006093968 A1 | 9/2006 |
| WO | WO2006110147 | 10/2006 |
| WO | WO2006130836 A2 | 12/2006 |
| WO | WO2007021647 A2 | 2/2007 |
| WO | WO2007028092 A2 | 3/2007 |
| WO | WO2008025405 A1 | 3/2007 |
| WO | WO2007038608 A1 | 4/2007 |
| WO | WO2007038609 | 4/2007 |
| WO | WO2007083288 A2 | 7/2007 |
| WO | WO2007092860 | 8/2007 |
| WO | WO2007120186 A2 | 10/2007 |
| WO | WO2007136660 A2 | 11/2007 |
| WO | WO2007140419 | 12/2007 |
| WO | WO2007140420 A2 | 12/2007 |
| WO | WO2008033309 A1 | 3/2008 |
| WO | WO2008040555 A2 | 4/2008 |
| WO | WO2008124603 A1 | 10/2008 |
| WO | WO2008125689 A1 | 10/2008 |

OTHER PUBLICATIONS

"Construction of hydraulic cuff colluders for blood vessels." Shoukas, Arin A., Department of Biomedical Engineering. Johns Hopkins University. 1976.

International Search Report dated Sep. 26, 2008 for International Application No. PCT/US07/75611 (2 pages).

International Search Report dated Sep. 9, 2008 for International Application No. PCT/US07/75608 (2 pages).

* cited by examiner

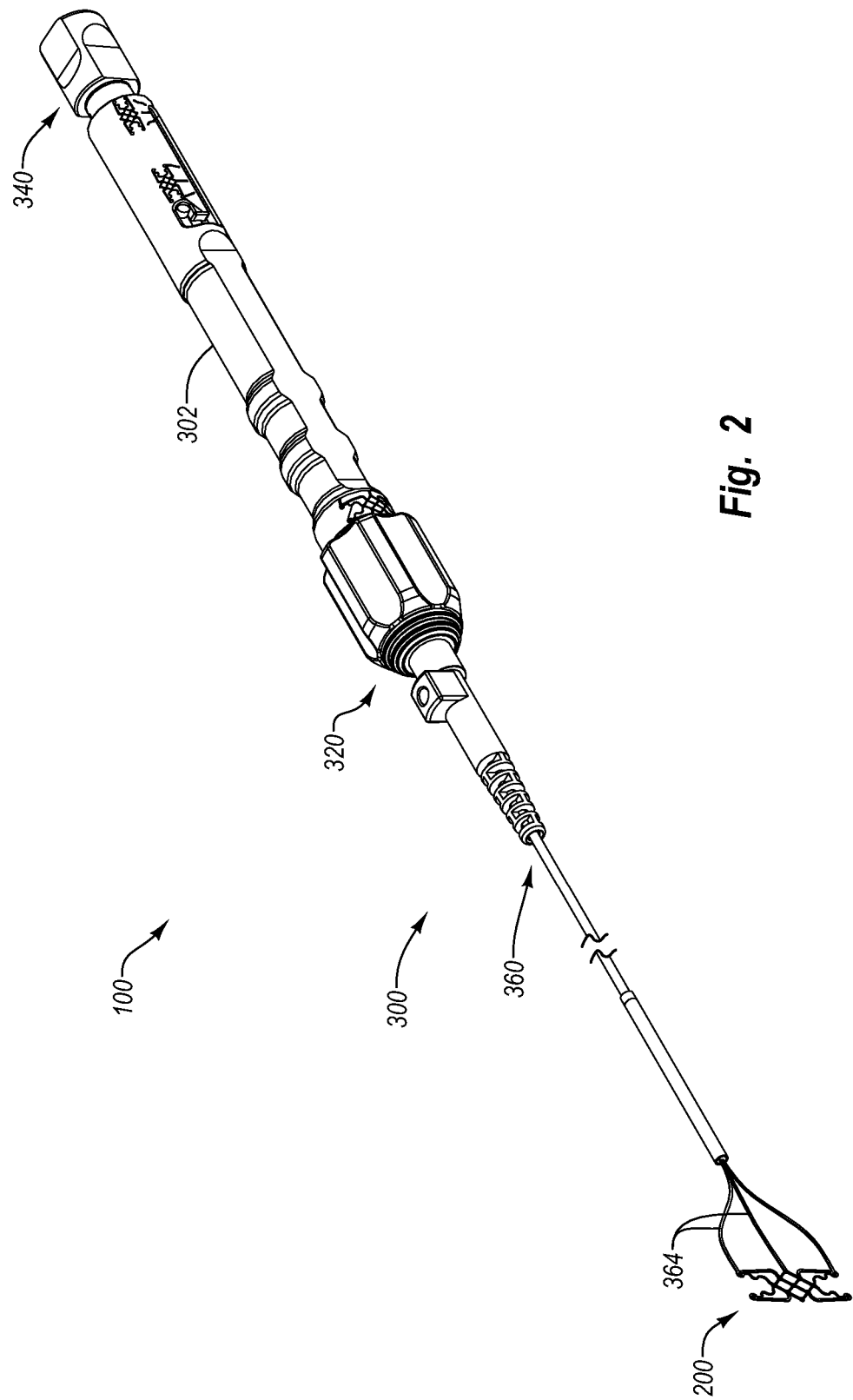

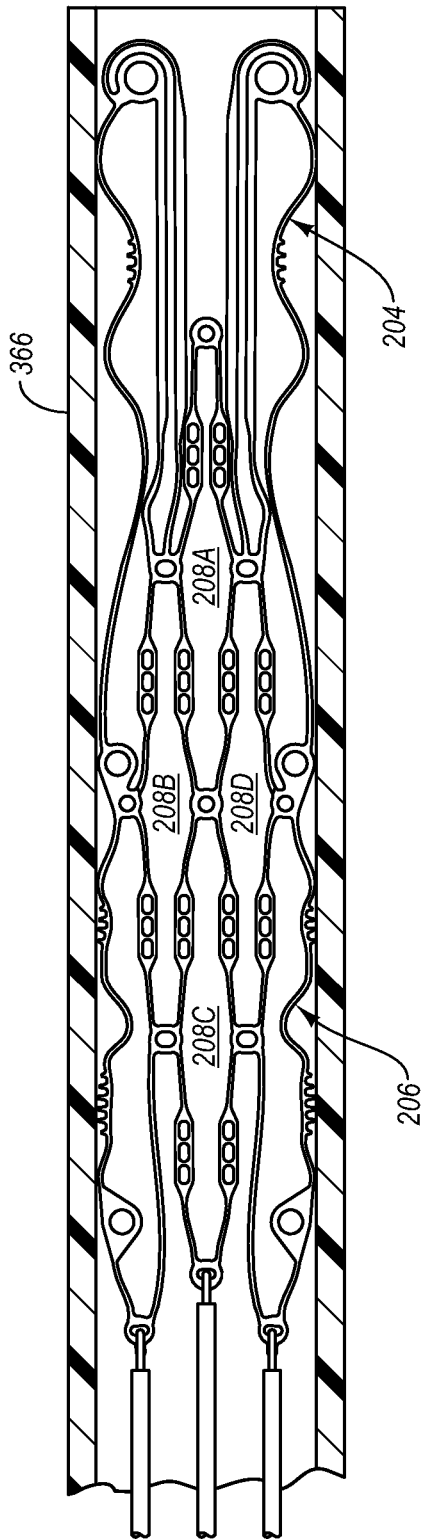
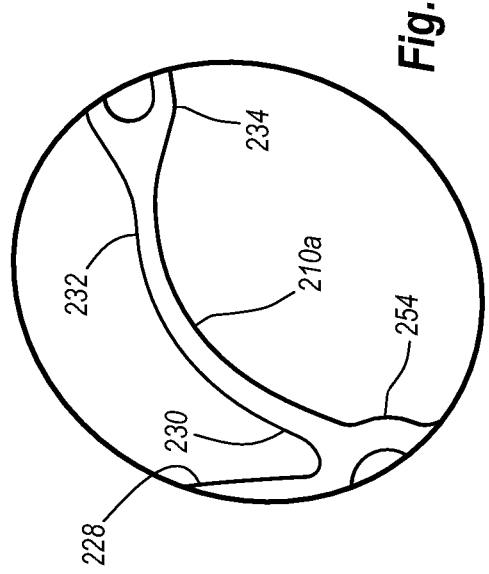
Fig. 3B
Fig. 3C

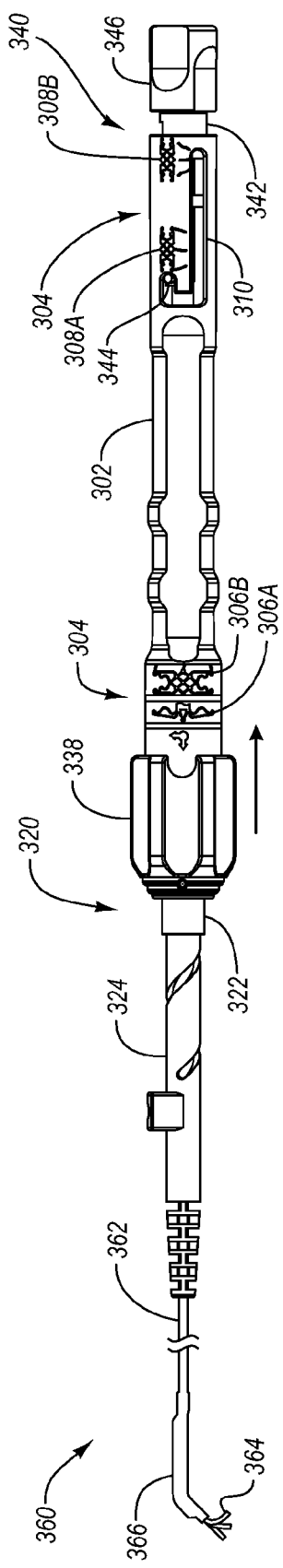
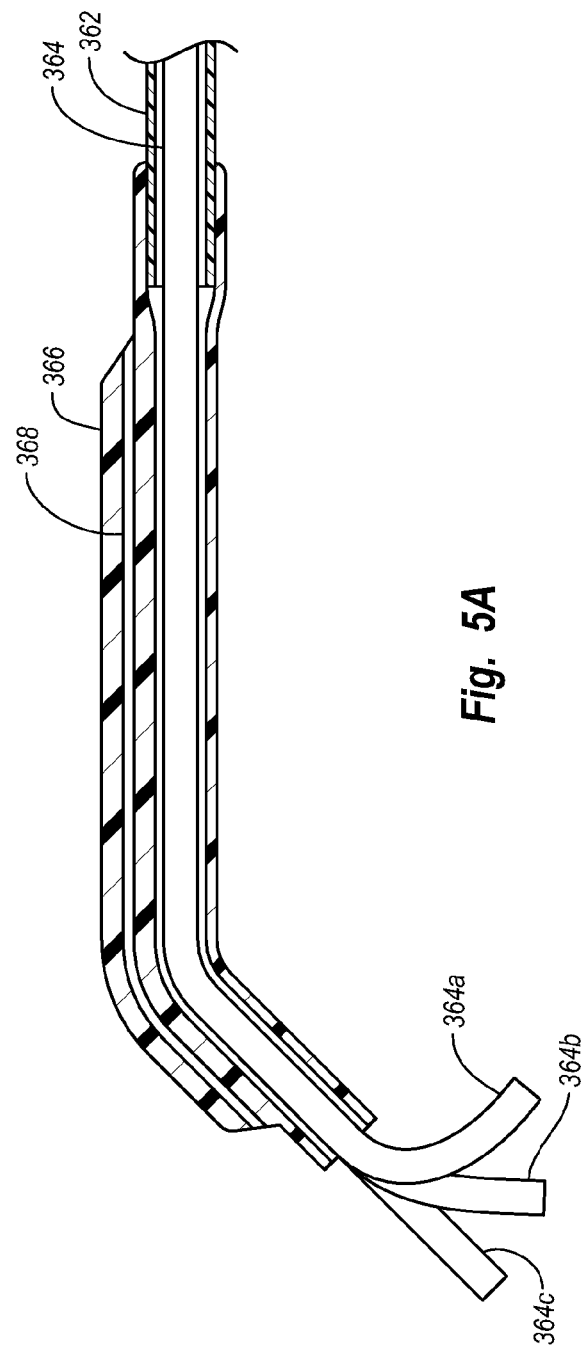
Fig. 4
Fig. 5A

SYSTEMS AND DEVICES FOR REDUCING THE SIZE OF AN INTERNAL TISSUE OPENING

CROSS-REFERENCE TO RELATED APPLICATIONS

This application claims the benefit of U.S. Provisional Application No. 60/821,947, filed Aug. 9, 2006, U.S. Provisional Application No. 60/821,949, filed Aug. 9, 2006, U.S. Provisional Application No. 60/829,507, filed Oct. 13, 2006, U.S. Provisional Application No. 60/866,047, filed Nov. 15, 2006, and U.S. Provisional Application No. 60/942,625, filed Jun. 7, 2007, the contents of each of which are hereby incorporated by reference in their entirety. This application relates to U.S. patent application Ser. No. 11/836,000, filed Aug. 8, 2007, titled DEVICES FOR REDUCING THE SIZE OF AN INTERNAL TISSUE OPENING, U.S. patent application Ser. No. 11/836,016, filed Aug. 8, 2007, titled DEVICES FOR REDUCING THE SIZE OF AN INTERNAL TISSUE OPENING, U.S. patent application Ser. No. 11/836,037, filed Aug. 8, 2007, titled DEVICES FOR REDUCING THE SIZE OF AN INTERNAL TISSUE OPENING, U.S. patent application Ser. No. 11/836,051, filed Aug. 8, 2007, titled SYSTEMS AND DEVICES FOR REDUCING THE SIZE OF AN INTERNAL TISSUE OPENING, U.S. patent application Ser. No. 11/836,026, filed Aug. 8, 2007, titled METHODS FOR DETERMINING CHARACTERISTICS OF AN INTERNAL TISSUE OPENING, and U.S. patent application Ser. No. 11/836,123, filed Aug. 8, 2007, titled METHODS, SYSTEMS AND DEVICES FOR REDUCING THE SIZE OF AN INTERNAL TISSUE OPENING, the contents of each of which are hereby incorporated by reference in their entirety.

BACKGROUND OF THE INVENTION

1. The Field of the Invention

The present invention relates generally to medical devices and methods of use for treating an internal tissue structure. More particularly, the present invention relates to medical devices, systems, and methods for reducing the size of an internal tissue opening.

2. The Relevant Technology

Physical malformations or defects that are present at birth can be detrimental and even lethal when left uncorrected. A PFO is an example of a cardiac birth defect that can be problematic and even result in death when combined with other factors such as blood clots or other congenital heart defects. A PFO occurs when an opening between the upper two chambers of the heart fail to close after birth.

Some of the problems associated with a PFO can occur when a blood clot travels from the right to the left atria of the heart through the PFO, and lodges in an artery that feeds blood to the brain. A blood clot in the left atrium can be passed through the aorta and travel to the brain or other organs, and cause embolization, stroke, or a heart attack. A PFO can be treated by being closed by a surgical procedure. Additionally, other similar defects (e.g. septal or otherwise) where some tissue needs to be closed in order to function properly can include the general categories of atrial-septal defects ("ASDs"), ventricular-septal defects ("VSD's") and patent ductus arteriosus ("PDA"), and the like.

FIGS. 1A-1C depict various views of a heart having a PFO. The heart 10 is shown in a cross-section view in FIG. 1A. In a normal heart 10, the right atrium 30 receives systemic venous blood from the superior vena cava 15 and the inferior vena cava 25, and then delivers the blood via the tricuspid valve 35 to the right ventricle 60. However, in the depicted heart 10 a septal defect, which is shown as a PFO 50, is present between right atrium 30 and left atrium 40.

The PFO 50 is depicted as an open flap on the septum between the heart's right atrium 30 and left atrium 40. In a normal heart 10, the left atrium 40 receives oxygenated blood from the lungs via pulmonary artery 75, and then delivers the blood to the left ventricle 80 via the mitral valve 45. In a heart 10 having a PFO 50 some systemic venous blood can also pass from the right atrium 30 through the PFO 50 and mixes with the oxygenated blood in left atrium 40, and then is routed to the body from left ventricle 80 via aorta 85.

During fetal development of the heart 10, the interventricular septum 70 divides the right ventricle 60 and left ventricle 80. In contrast, the atrium is only partially partitioned into right and left chambers during normal fetal development, which results in a foramen ovale fluidly connecting the right and left atrial chambers. As shown in FIG. 1B, when the septum primum 52 incompletely fuses with the septum secundum 54 of the atrial wall, the result can be a tunnel 58 depicted as a PFO 50.

FIG. 1C provides a view of the crescent-shaped, overhanging configuration of the septum secundum 54 from within the right atrium 30 in a heart 10 having a PFO 50. The septum secundum 54 is defined by its inferior aspect 55, corresponding with the solid line in FIG. 1C, and its superior aspect 53 represented by the phantom line, which is its attachment location to the septum primum 52. The septum secundum 54 and septum primum 52 blend together at the ends of the septum secundum 54. The anterior end 56a and posterior end 56p are referred to herein as "merger points" for the septum secundum 54 and septum primum 52. The length of the overhang of the septum secundum 54, which is the distance between superior aspect 53 and inferior aspect 55, increases towards the center portion of the septum secundum as shown.

The tunnel 58 between the right atrium 30 and left atrium 40 is defined by portions of the septum primum 52 and septum secundum 54 between the merger points 56a and 56p which have failed to fuse. The tunnel 58 is often at the apex of the septum secundum 54 as shown. When viewed within right atrium 30, the portion of the septum secundum 54 to the left of tunnel 58, which is referred to herein as the posterior portion 57p of the septum secundum, is longer than the portion of the septum secundum 54 to the right of tunnel 58, which is referred to herein as the anterior portion 57a of the septum secundum 54. In addition to being typically longer, the posterior portion 57p also typically has a more gradual taper than the anterior portion 57a as shown. The anterior pocket 59a is the area defined by the overhang of the anterior portion 57a of the septum secundum 54 and the septum primum 52, and it extends from the anterior merger point 56a toward the tunnel 58. Similarly, the posterior pocket 59p is the area defined by the overhang of the posterior portion 57p of septum secundum 54 and the septum primum 52, and it extends from the posterior merger point 56p toward the tunnel 58.

Conventional treatments for PFO, and other related conditions have generally involved invasive surgery, which also presents a risks to a patient. Although there are some less invasive treatments for PFO, such treatments have been less efficient at closing the PFO opening than techniques involving invasive surgery.

BRIEF SUMMARY OF THE INVENTION

The invention relates to a medical system, devices and methods of use for reducing the size of an internal tissue opening, such as a Patent Foramen Ovale ("PFO"). In one embodiment of the invention, the medical system can include a closure device and an associated delivery device. The medical system can be configured to enable a practitioner to selectively position and deploy the closure device in an internal tissue opening to approximate, or in other words bring together the tissue of the opening.

According to one embodiment of the invention, the closure device can include a multi-cellular body portion operatively associated with a first anchor and a second anchor. The multi-cellular body portion can be configured to enable the closure device to collapse into a relatively narrow non-deployed orientation and expand into a deployed or expanded orientation without plastic deformation or failure of the closure device. The first and second anchors can be configured to engage at least a portion of a wall of the internal tissue opening and/or tissue, such as tunnel tissue, of the opening. In one embodiment of the invention, the closure device can be a non-tubular, substantially flat stent.

In one embodiment of the invention the closure device can include an ingrowth material to facilitate tissue growth. The closure device can also include one or more indicators to facilitate the estimation of the position and/or orientation of the closure device with respect to the internal tissue opening.

In accordance with the present invention, the delivery device can include a delivery assembly, an actuating assembly, and a release assembly operatively associated with a handle body. In one embodiment of the invention, the delivery assembly facilitates selective delivery of the closure device from the delivery device, and is operatively associated with the actuating assembly and the release assembly. The actuating assembly interacts with the handle body to selectively deploy the closure device from the delivery assembly. In one embodiment of the invention, the actuating assembly can be configured to deploy at least a portion of the closure device by a first movement and deploy a second portion of the closure device by a second movement. The release assembly can be linked to the handle body to facilitate detachment of the closure device from the delivery device.

In one embodiment, the closure device is linked to the delivery device by one or more tethers and one or more wires, the tethers being coupled to the handle body and the wires being coupled to a biasing member of the release assembly. The tethers can be configured to receive a portion of the closure device therein to facilitate securement of the closure device to the delivery device. The wires can be detachably coupled to the closure device to enable selective detachment of the closure device from the delivery device by movement of the biasing member.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 2 illustrates a perspective view of an embodiment of a medical system according to the present invention;

FIG. 3B illustrates an embodiment of a closure device in a non-deployed orientation according to the present invention;

FIG. 3C illustrates a cut-out view of a portion of a closure device according to the present invention;

FIG. 4 illustrates an embodiment of a delivery device according to the present invention;

FIGS. 5A-5C illustrate cross-sectional views of a delivery device according to the present invention;

DETAILED DESCRIPTION OF THE PREFERRED EMBODIMENTS

Figure 1B:
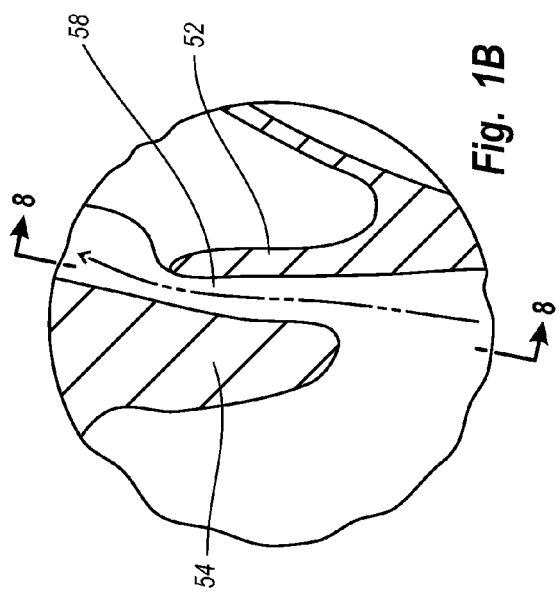
FIGS. 1A-1C illustrate exemplary views of a heart having a Patent Foramen Ovale.
Figure 1C:
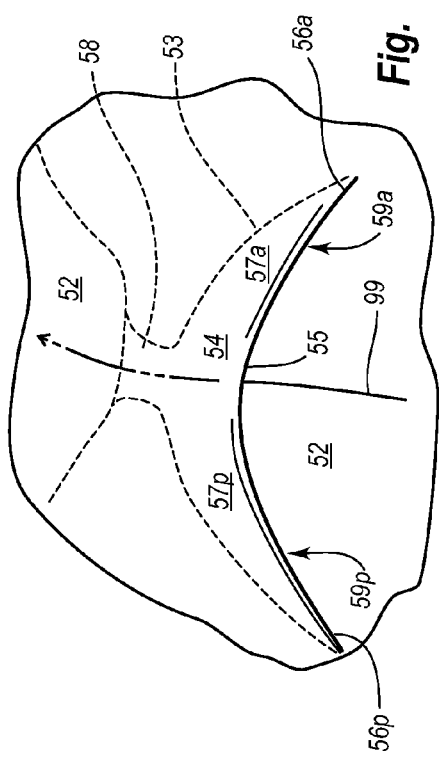
Figure 1A:
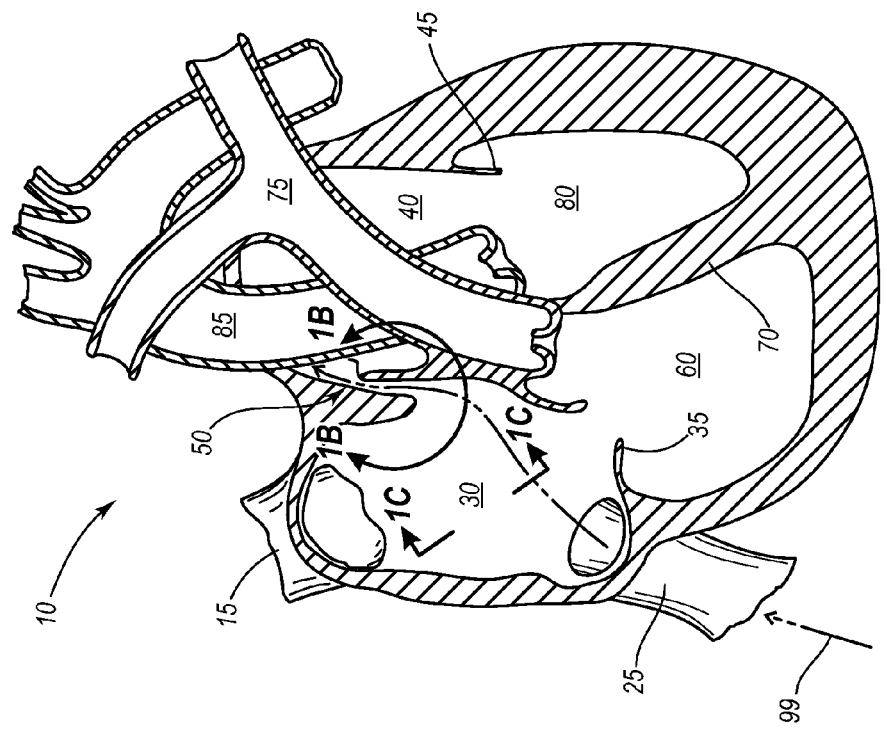

The present invention extends to medical systems, methods, and apparatus for reducing the size of an internal tissue opening. By way of explanation, the devices disclosed herein can be used to treat a variety of internal tissue openings, such as a left atrial appendage, paravalvular leaks, PDA's, and VSD's, for example. Although, for purposes of simplicity, frequent reference is made herein to reducing the size of or closing an opening in heart tissue known as Patent Foramen Ovale ("PFO"). Accordingly, it will be understood that references to PFO openings are not limiting of the invention.

In the following description, numerous specific details are set forth to assist in providing an understanding of the present invention. In other instances, aspects of delivery and/or closure devices, or medical devices in general have not been described in particular detail in order to avoid unnecessarily obscuring the present invention. In addition, it is understood that the drawings are diagrammatic and schematic representations of certain embodiments of the invention, and are not limiting of the present invention, nor are they necessarily drawn to scale.

Introduction of Medical System 100

FIG. 2 is a perspective view of a medical system 100 configured to facilitate closure of an internal tissue opening according to one embodiment of the present invention. In the illustrated embodiment, the medical system 100 comprises a closure device 200 adapted to reduce the size of the internal tissue opening, and a delivery device 300 adapted to facilitate placement and deployment of the closure device 200 with respect to the internal tissue opening. The medical system 100 of the present invention can provide benefits. For example, the medical system 100 can be configured to be used with different sizes, shapes and types of internal tissue openings. Furthermore, the medical system 100 can provide various safety measures to increase the safety and effectiveness of positioning the closure device 200. In addition, the medical system 100 can be configured to provide distributed lateral force to tissue of the internal tissue opening.

In the illustrated embodiment, delivery device 300 comprises a handle body 302, an actuating assembly 320 operatively associated with handle body 302, a release assembly 340 operatively associated with the handle body 302 and a delivery assembly 360 operatively associated with the actuating assembly 320, the release assembly 340 and the handle body 302. Handle body 302 can be configured to provide a gripping surface for a user. Handle body 302 can be used to position closure device 200, as well as facilitate deployment of the closure device 200 from the delivery assembly 360. Actuating assembly 320 can be moved with respect to handle body 302 to selectively deploy portions of the closure device 200 from the delivery assembly 360, as will be discussed more fully herein below.

Release assembly 340 can be operatively associated with the handle body 302 to enable selective detachment of closure device 200 from the delivery assembly 360. Delivery assembly 360 can house closure device 200 in a non-deployed or constrained orientation, such as illustrated in FIG. 3B for example, and facilitate deployment of closure device 200. Delivery assembly 360 can include one or more tethers 364 linked to the closure device 200 to facilitate selective detachment of the closure device 200 from the delivery device 300.

Closure Device 200

Figure 3A:
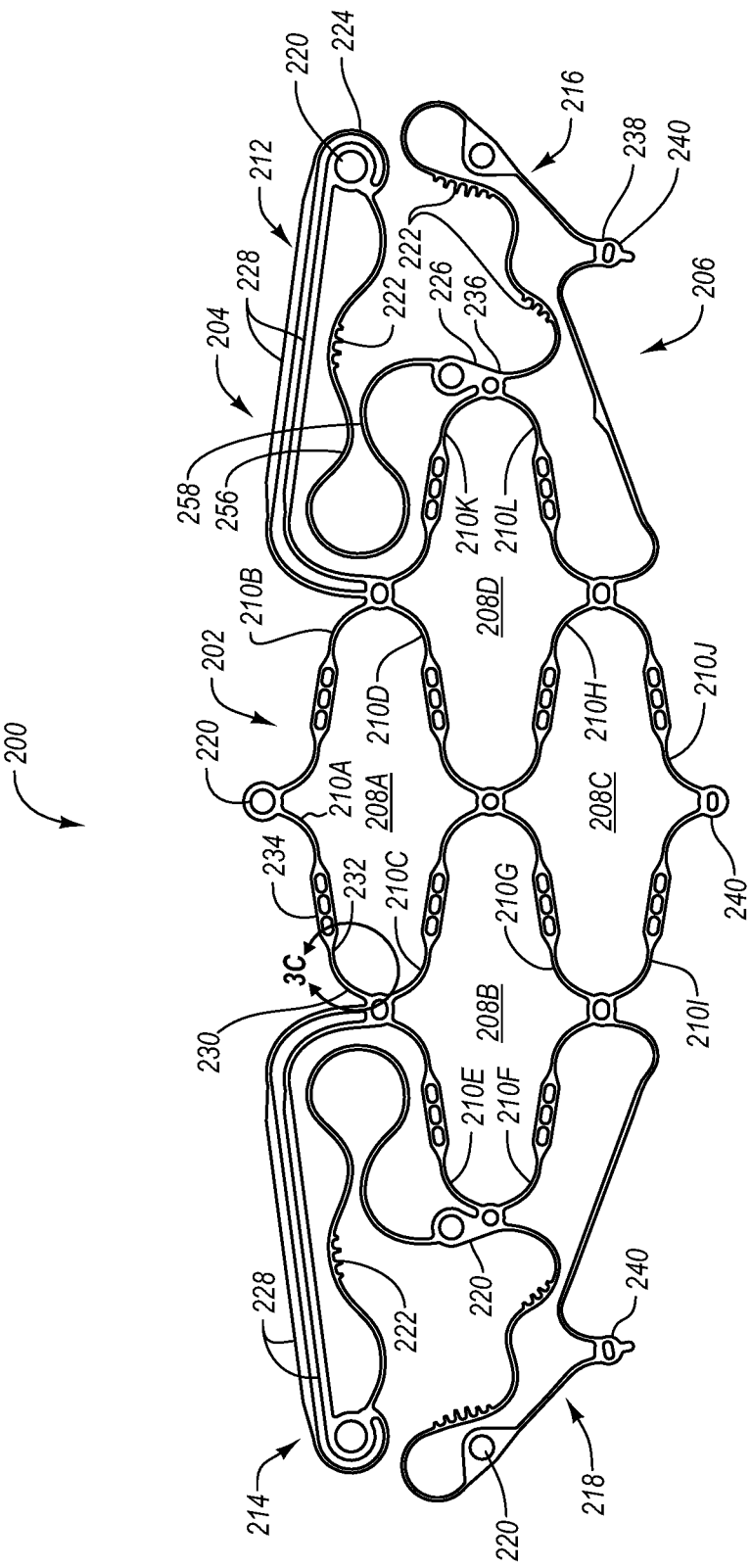
FIG. 3A illustrates an embodiment of a closure device according to the present invention.

With reference to FIG. 3A, the closure device 200 is illustrated in a fully deployed, expanded, relaxed or non-constrained orientation. According to one embodiment of the invention, the closure device 200 can be configured to reduce the size of an internal tissue opening so as to close the internal tissue opening. In one embodiment, the closure device 200 can reduce the size of an internal tissue opening by approximating, or in other words bringing together tissue of the internal tissue opening, such as tunnel tissue in a PFO. The closure device 200 can approximate tissue by applying lateral force to tissue of the internal tissue opening, as will be discussed more fully herein after. Also, the closure device 200 can be configured to enable a user to estimate the position and/or orientation of the closure device 200 with respect to an internal tissue opening, during and after positioning of the closure device 200 in the internal tissue opening.

Figure 11B:
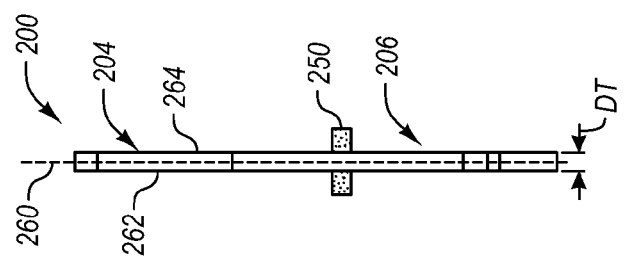
FIG. 11B illustrates a side view of the closure device of FIG. 11A.

According to one embodiment of the invention, the closure device 200 can be a non-tubular stent. The closure device 200 can be configured to assume a substantially flat configuration, or in other words be configured to be substantially planar, such as illustrated in FIGS. 3A and 11B for example. Furthermore, the closure device 200 can be configured to resist movement out of plane, such as plane 260 of FIG. 11B. However, the closure device 200 may bend out of plane when positioned in a tissue opening.

The closure device 200 according to one embodiment of the invention has many advantages. For example, the closure device 200 can be configured to be reliable and compliant. The configuration of the closure device 200 can enable the closure device 200 to be movable between a non-deployed orientation and a deployed orientation without causing failure or plastic deformation of the closure device 200. The closure device 200 can be used to close various types, shapes and sizes of internal tissue openings. Furthermore, the closure device 200 can accommodate for a range of PFO tunnel lengths, for example. Also, the closure device 200 can be partially or fully deployed from or received back into the delivery device 300. Closure device 200 can be configured to substantially conform to the size and shape of a tissue opening. For example, the undulations on the distal and proximal anchors can enable the anchors to substantially, or to a certain degree, conform to the anatomy of a tissue opening.

Generally, the closure device 200 can have a substantially flat aspect having a length and height greater than its depth or depth thickness. For example, in one embodiment, the closure device 200 has an overall length of 22 mm, a height of 7.5 mm and a depth thickness of 0.4 mm. According to one embodiment of the present invention, when the closure device 200 is in the relaxed or completely expanded orientation, as illustrated in FIG. 3A, the distance between the opposing ends of the proximal anchor 218 can be about 22 mm, the distance between the most proximal attachment member 240 of the body portion 202 and the most distal indicator 220 of the body portion 202 can be about 7.5 mm, and the depth thickness, designated as DT in FIG. 11B, of the closure device 200 can be about 0.4 mm.

Furthermore, the majority of segments comprising the closure device 200 can have a thickness or width that is substantially less than the depth thickness of the segments. The closure device 200 can resist out of plane movement due to the size and configuration of the segments. For example, the closure device 200 can be configured to assume a substantially flat configuration in a first plane. The configuration of the segments, for example the segments having a certain depth thickness, can facilitate the closure device 200 resisting movement out of the first plane in a manner similar to an I beam resisting bending in the direction of the web of the beam. The first plane can be plane 260 as illustrated in FIG. 11B.

Also, the closure device 200, according to one embodiment of the invention, can have a unitary construction. For example, the closure device 200 can be cut from a single piece of material, such as cut by a laser, thereby removing the need to assemble or join different segments together. A unitary construction can provide advantages, such as ease of manufacturing and reliability. For example, assembly is not required for a closure device having a unitary construction. Also, a closure device having a unitary construction may not include distinct elements or segments which require joining by joints, thereby reducing a likelihood of failure. The closure device 200 can be made from a super-elastic material, such as a super-elastic metal or a super-elastic polymer. Furthermore, the closure device 200 can be made from NiTiNol, stainless steel alloys, magnesium alloys, and polymers including bioresorbable polymers.

In some embodiments according to the present invention, the closure device can be formed by utilizing a pressurized stream of water, such as a water jet, to remove material from a piece of material to form the closure device. Furthermore, it is contemplated that the closure device can be formed by utilizing one or more of the following: die casting, chemical etching, photolithography, electrical discharge machining, or other manufacturing techniques. It is contemplated that the closure device can be formed through use of a mill or some other type of device adapted to remove material to form a desired shape.

It will be appreciated by one of ordinary skill in the art in view of the disclosure provided herein that the closure device 200 can comprise multiple segments joined together by a known joining process, such as by an adhesive, by interference fits, crimping, by fasteners, or a weld, or some combination thereof. For example, in one embodiment, the closure device can include multiple segments joined together by various welds to form a closure device according to the present invention. In other embodiments, the segments can be joined together by a plurality of means, such as by the combination of welding, fasteners, and/or adhesives. The segments can be a wire or multiple joined or rolled wires crimped together or joined by a joining process to form the closure device 200.

In the illustrated embodiment, the closure device 200 includes a body portion 202, a first anchor 204 operatively associated with the body portion 202 and a second anchor 206 operatively associated with the body portion 202. The body portion 202 can be configured to facilitate application of lateral force against tissue of an internal tissue opening. Also, the body portion 202 can be configured to enable the closure device 200 be movable between a non-deployed and deployed orientation. For example, the closure device 200 can be configured to be self-expanding from the constrained or non-deployed orientation, as illustrated in FIG. 3B for example, to the relaxed orientation, as illustrated in FIG. 3A. In other words, the closure device 200 can have a preferential orientation, such that movement of the closure device 200 from a first orientation to a second orientation can create internal stresses in the closure device 200. These internal stresses can serve to bias the closure device 200 to the first orientation. For example, in one embodiment, the closure device 200 can have a preferential orientation of the relaxed or fully deployed orientation as illustrated in FIG. 3A. In this embodiment, movement of the closure device 200 to a constrained orientation, such as illustrated in FIG. 3B for example, can create internal stresses in the closure device 200, thereby creating in the closure device 200 a bias to return to the relaxed orientation.

In the illustrated embodiment, body portion 202 includes one or more cells 208 defined by a plurality of segments 210. The body portion 202 can include one or more apertures. In one embodiment, an aperture is defined by the cell 208, or in other words by the plurality of segments 210. In one embodiment, segment 210 can be a strut or a body support segment. Cells 208 can be distinct, or can be at least partially defined by a common segment. For example, cell 208A, as the distal most cell, and cell 208C, as the proximal most cell of body portion 202, are distinct and defined by distinct segments 210 with respect to each other. However, cell 208B is partially defined by a segment 210C which also defines a portion of cell 208A. Similarly, cell 208B is partially defined by a segment 210G which also partially defines cell 208C. Likewise, cell 208D shares a segment 210D with cell 208A and shares a segment 210H with cell 208C.

Segments 210 can be shaped and configured to have a substantially uniform stress at any given point along a certain length, when the segment 210 is deflected. For example, segment 210A can include a first portion 230 having a width or thickness greater than a second portion 232, wherein the width or thickness decreases from the first portion 230 to the second portion 232, or in other words is tapered, in a manner which provides for substantially uniform stress levels along the certain length. In other embodiments, segments can have a substantially constant width along their length.

FIG. 3C is a cut-out view of a portion of the closure device 200, including the first portion 230 and the second portion 232 of segment 210A. In the illustrated embodiment, the width or thickness of the segment 210A varies along the portion of the segment 210A from the location where segment 210A extends from the portion 254 which joins segment 210A to segment 210C to the intermediate portion 234. As the closure device 200 moves between an expanded or otherwise related orientation and a constrained or otherwise collapsed orientation, the segments 210 are deflected, with the highest levels of stress in the segment 210 being concentrated at the joining portion 254 and decreasing towards the intermediate portion 234. The segments 210 can be configured in a manner so as to have a substantially equal stress level along the length of the segment 210 between the joining portion 254 and the intermediate portion 234. The uniform stress level can be accomplished by having the width of the segment 210 vary from the first portion 230 to the second portion 232 in a calculated manner. In one embodiment, the width of the first portion 230 of the segment can be about 0.1 mm and the taper to a width of about 0.05 mm at the second portion 232 of the segment.

In other embodiments, the uniform stress level can be accomplished by utilizing a gradient of material having varying properties. In other embodiments, the segment 210 can have varying widths along its length and comprise a gradient of material sufficient to achieve a substantially uniform stress level between the first portion 230 and the second portion 232 of the segment. In the illustrated embodiment, the first portion is adjacent the joining portion 254 and the second portion is adjacent the intermediate portion 234. In yet additional embodiments, the joints of the interconnecting segments can include a biasing member, such as a spring, thereby enabling the segments to move relative to each other to collapse or expand the closure device 200. Furthermore, the biasing member of the joint can cause the segments to have a preferential orientation with respect to each other.

With continued reference to FIG. 3A, segments 210 can also be configured to have a rectangular cross-section. In other embodiments, segments 210 can have an oval shaped cross section. In yet another embodiment, sections 210 can have a round or rounded cross section. Furthermore, in one embodiment, the ratio, or aspect ratio, of the thickness or width to the depth thickness of the first and second portions 230, 232 can range between at least about 1:2 to about 1:20. In one embodiment, the aspect ratio of the width to the depth thickness of the first portion 230 can be at least 1:2 and the ratio of the width to the depth thickness of the second portion 232 can be at least 1:4. In an alternative embodiment, the aspect ratio of the first portion 230 can be about 1:4 and the aspect ratio of the second portion 232 can be about 1:8. In this manner, the closure device 200 can substantially resist out of plane movement, while allowing in-plane movement during reorientation of various portions of the closure device 200.

Segments 210 can be configured to be compliant. Compliancy of segments 210 can enable cells 208, and thus the body portion 202, to be oriented in various orientations. For example, body portion 202 can be oriented, or in other words moved, between a non-deployed orientation, such as illustrated in FIG. 3B, and a fully deployed orientation, such as illustrated in FIG. 3A. The compliancy of segments 210 can facilitate the accommodation by the closure device 200 of a variety of types, shapes and sizes of internal tissue openings. For example, the size and configuration of the first and second anchors 204, 206 and the body portion 202 can enable the closure device 200 to accommodate varying sizes, shapes and types of internal tissue openings. In one implementation, the first anchor 204 can engage wall tissue of an internal tissue opening and the second anchor 206 can engage only the tunnel tissue of the internal tissue opening to approximate tissue. In an alternative implementation where the internal tissue opening has a shorter tunnel length, the second anchor 206 can engage the tunnel tissue and an opposing wall of the internal tissue opening to approximate tissue.

Segments 210 can include an intermediate portion 234 configured to facilitate securement of ingrowth materials to the closure device 200, or can be used as an indicator 220 to facilitate estimation of the position of the closure device 200 with respect to an internal tissue opening. Furthermore, intermediate portion 234 can be configured to facilitate measuring of a characteristic of an internal tissue opening. In one embodiment, intermediate portion 234 can include one or more apertures. The apertures can be configured to receive a securing element, such as a thread, therethrough to facilitate securing an ingrowth material to the closure device 200. Intermediate portion 234 can be configured to be stiffer or more rigid than first portion 230, second portion 232, or both. A stiffer intermediate portion 234 can increase the reliability of segments 210.

In another embodiment, the intermediate portion 234 can include an indicator 220, such as a dense metallic rivet or concentration of dense material, for use in estimating the orientation and/or position of the closure device 200. Understanding of the orientation and/or position of the closure device 200 can facilitate estimating a physical characteristic of an internal tissue opening and/or the relative position of the closure device 200 with respect to the internal tissue opening. For example, if the distance between the indicators 220 is known, a practitioner can estimate a physical characteristic, such as the opening or tunnel width, by determining the new distance between the indicators 220 when the closure device 200 is positioned in the tissue opening. Similarly, indicators 220 can be positioned on the first and second anchors 04, 206. The indicators 220 can be configured and arranged on the closure device 200 such that when the first anchor 204 is deployed the indicators 220 are substantially aligned. In this manner, a practitioner can estimate whether the first anchor 204 has fully deployed.

In some cases, it may be difficult to view the closure device 200 in the event the closure device 200 is at a skewed angle with respect to the viewing plane, such as a fluoroscope. When the closure device 200 is skewed in this manner, it can be difficult to determine accurately the distance of interest. However, when various distances between indicators is known, a user can use the known distances to calculate the distances of interest by using geometry.

In one embodiment, segments 210 along a similar or common lateral plane can have substantially equal lengths. Substantially equal lengths of segments 210 in this manner can enable body portion 202 to be moved between the non-deployed and deployed orientation without failure of the segments 210. For example, in one embodiment, segments 210A and 210B have substantially the same length, segments 210E, 210C, 210D, and 210K have substantially the same length, segments 210F, 210G, 210H and 210L have substantially the same length, and segments 210I and 210J have substantially the same length. In this configuration, body portion 202 can be collapsed or oriented into the non-deployed orientation, as illustrated in FIG. 3B, without causing damage to the body portion 202 of closure device.

The closure device 200 can be configured to have a preferential orientation of the fully deployed orientation as illustrated in FIG. 3A. As the closure device 200 is deployed from the delivery device 300, the configuration of closure device 200 can cause the closure device 200 to preferentially move toward the fully deployed orientation. Thus, as the closure device 200 is deployed in an internal tissue opening, the preferential orientation of the closure device 200 can cause the closure device 200 to apply lateral force to the tissue of the internal tissue opening. In other words, the body portion 202, first anchor 204 and the second anchor 206 are deflected by an applied force in order to reorient the closure device 200 from the fully deployed orientation to a non-deployed orientation, for example. In this manner, the closure device 200, because of the deflection of the body portion 202, first anchor 204 and the second anchor 206, will have tendency to return to the fully deployed orientation. When the closure device 200 is positioned in an internal tissue opening, the deflected body portion 202, first anchor 204 and the second anchor 206 can have a tendency to apply a lateral force to tissue of the opening as the closure device 200 attempts to return to the fully deployed orientation.

Body portion 202 can be operatively associated with the first anchor 204 and the second anchor 206. First and second anchors 204, 206 can be configured to move between a deployed and non-deployed orientation. First and second anchors 204, 206 can be configured to apply lateral force to tissue of an internal tissue opening, and to engage and/or contact a portion of wall tissue and/or tunnel tissue of an internal tissue opening. In one embodiment, the first anchor 204 can be a left atrial anchor, and the second anchor 206 can be a right atrial anchor.

In the illustrated embodiment, the first anchor 204 can include a first anchor segment 212 and an opposing second anchor segment 214. Likewise, the second anchor 206 can include a first anchor member 216 and an opposing second anchor member 218. The first anchor segment 212 can be configured to move relative to the second anchor segment 214. Likewise, the first anchor member 216 can be configured to move relative to the second anchor member 218. In this manner, the closure device 200 can accommodate for a variety of types, shapes and sizes of internal tissue openings. The first anchor segment 212 and the second anchor segment 214 can be configured to be substantially similar in size, shape and configuration. As such, reference to the configuration and/or function of one of the first or second anchor segments can apply to the other anchor segment. In one embodiment of the invention, the first anchor 204 and/or the second anchor 206 can include one or more undulations. The undulations can facilitate reorienting or movement of the anchors with respect to the body portion 202, for example, from a deployed to a non-deployed configuration. Furthermore, the undulations can facilitate the anchor substantially conforming to the anatomy of the tissue opening.

The first anchor segment 212 can include a distal end 224 and a proximal end 226. The first anchor segment 212 can be defined by various segments and can include reinforced segments 228 and one or more engaging members 222. For example, in the illustrated embodiment, the first anchor segment 212 is at least partially defined by segment 210K of cell 208D. The engaging members 222 can be microposts or tines configured to contact and/or engage tissue. The engaging members 222 can include a sharp tip or can be blunt. The engaging members 222 can be configured to provide a degree of surface texture in order to increase engagement of the first anchor 204 with tissue.

The first anchor segment 212 can be configured to be moved between a non-deployed orientation, as illustrated in FIG. 3B, and a fully deployed orientation, as illustrated in FIG. 3A. The first anchor segment 212 can be configured such that the distance from the proximal end 226 to the distal end 224 of the segment which includes the engaging members 222 is substantially equal to the distance from the proximal end 226 to the distal end 224 of the segment which includes the reinforced segments 228 and segment 210K. The second anchor segment 214 can be configured similar to the first anchor segment 212.

First anchor segment 212 can be configured to define a closed periphery. For example, first anchor segment 212 can include the reinforced segment 228 extending from the body portion 202 to the segment having the engaging members 222 which is connected to segments 210K, 210L to define a closed periphery with segment 210K. Furthermore, two reinforced segments 228 can extend from the joining portion 254 of the body portion 202 and join together near the distal end 224 of the first anchor 204. As such, there are multiple anchor portions extending from the body portion 202. In this manner, anchors of the present invention are reinforced to provide greater rigidity and strength to facilitate stabilization and maintenance of the closure device 200 within a tissue structure.

First anchor member 216 can include a distal end 236 and a proximal end 238. The first anchor member 216 can be defined by various segments and can include one or more engaging members 222. For example, in the illustrated embodiment, the first anchor member 216 is at least partially defined by segment 210L of cell 208D. The engaging members 222 can be microposts or tines configured to contact and/or engage tissue. The engaging members 222 can include a sharp tip or can be blunt. The engaging members 222 can be configured to provide a degree of surface texture to increase engagement of the second anchor 206 with tissue.

It will be understood by one of ordinary skill in the art in view of the disclosure provided herein that the engaging members 222 can vary in size and shape, and can be positioned at various locations on the closure device 200. In alternative embodiments, one or more engaging members can extend out of plane of the closure device so as to contact tissue which is perpendicular, for example, to the substantially flat plane, such as plane 260 of FIG. 11B, of the closure device 200.

The first anchor member 216 can be configured to be moved between a non-deployed orientation, as illustrated in FIG. 3B, and a fully deployed orientation, as illustrated in FIG. 3A. The first anchor member 216 can be configured such that the distance from the proximal end 238 to the distal end 236 of the segment which includes the engaging members 222 is substantially equal to the distance from the proximal end 238 to the distal end 236 of the segment which includes segment 210L. In this manner, first anchor member 216 can be detachably coupled to the delivery device 300 when in a non-deployed orientation inside the delivery device 300 as illustrated in FIG. 3B. The second anchor member 218 can be configured similar to the first anchor member 216.

The first anchor segment 212 can also include a first portion 256 and a second portion 258 configured to facilitate engagement of the internal tissue opening. For example, first anchor segment 212 can be configured to include one or more undulations causing the first portion 256 to be positioned in close proximity with second portion 258. In this manner, as tissue is positioned between the first and second portions 256, 258, the configuration of the first anchor segment 212 can engage, or to some degree, pinch the tissue therebetween to facilitate maintenance of the position of the closure device 200 with respect to the tissue opening.

The closure device 200 can also include attachment members 240 for use in detachably linking the closure device 200 to the delivery device 300, as will be discussed more fully herein after. The attachment members 240 can include an aperture 242 for use in facilitating the linking of the closure device 200 to the delivery device 300.

FIG. 3B illustrates the closure device 200 in a non-deployed or constrained orientation. The configuration of the body portion 202, and the first and second anchors 204, 206 enables the closure device 200 be reoriented from the fully deployed and preferential orientation, as illustrated in FIG. 3A, to the non-deployed or collapsed orientation as illustrated. In the collapsed or non-deployed orientation, the first anchor 204 extends distally and the second anchor 206 extends proximally, with the attachment members 240 being the proximal most portions of the second anchor 206 and the body portion 202.

In the illustrated embodiment, the closure device 200 is positioned inside of a delivery portion 366 of the delivery device 300. The configuration of the closure device 200 can cause portions of the closure device to apply force to the wall of the delivery portion 366 due to the preferential orientation of the closure device 200. The closure device 200 is configured to be received into and deployable from the delivery portion 366.

Delivery Device 300

FIG. 4 illustrates one embodiment of the delivery device 300. In the illustrated embodiment, the delivery assembly 360 includes a catheter 362 having a delivery portion 366, and a plurality of tethers 364 at least partially housed by the catheter 362. The tethers 364 can be configured to facilitate selective detachment of the closure device 200 from the delivery device 300. The delivery portion 366 can be configured to receive the closure device 200 therein. The catheter 362 can be coupled to the actuating assembly 320, such that movement of the actuating assembly 320 can cause movement of the catheter 362.

In the illustrated embodiment, the actuating assembly 320 includes a first member 322 operatively associated with the handle body 302, a second member 324 operatively associated with the first member 322 and the handle body 302, and a knob 338 linked to the first member 322. The actuating assembly 320 can be utilized by a user to selectively deploy the closure device 200 from the catheter 362.

The handle body 302 can include indicia 304 to enable a user to estimate the degree of deployment of the closure device 200 from the delivery device 300, as well as predict detachment of the closure device 200 from the delivery device 300. For example, indicia 304 can include deployment indicia 306 and release indicia 308. Deployment indicia 306 can be utilized to enable a user to estimate the degree of deployment of the closure device 200 from the catheter 362, and the release indicia 308 can be utilized to predict the detachment of the closure device 200 from the delivery device 300. The handle body 302 can also include a release pin groove 310. The release pin groove 310 can be operatively associated with the release assembly 340 to facilitate the selective detachment of the closure device 200 from the tethers 364.

According to one embodiment of the invention, the release assembly 340 can include a biasing member 342 operatively associated with the handle body 302 to facilitate detachment of the closure device 200. A release knob 346 can be provided to manipulate the position of biasing member 342 in order to release or detach the closure device 200. In one embodiment, the release knob 346 is coupled to the biasing member 342, such that movement of the release knob 346 can cause movement of the biasing member 342. The biasing member 342 can include a release pin 344 configured to be received in, influenced by and movable in the release pin groove 310. In this manner, release pin groove 310 can restrict, and thereby influence the movement of the biasing member 342 with respect to the handle body 302.

Figure 10A:
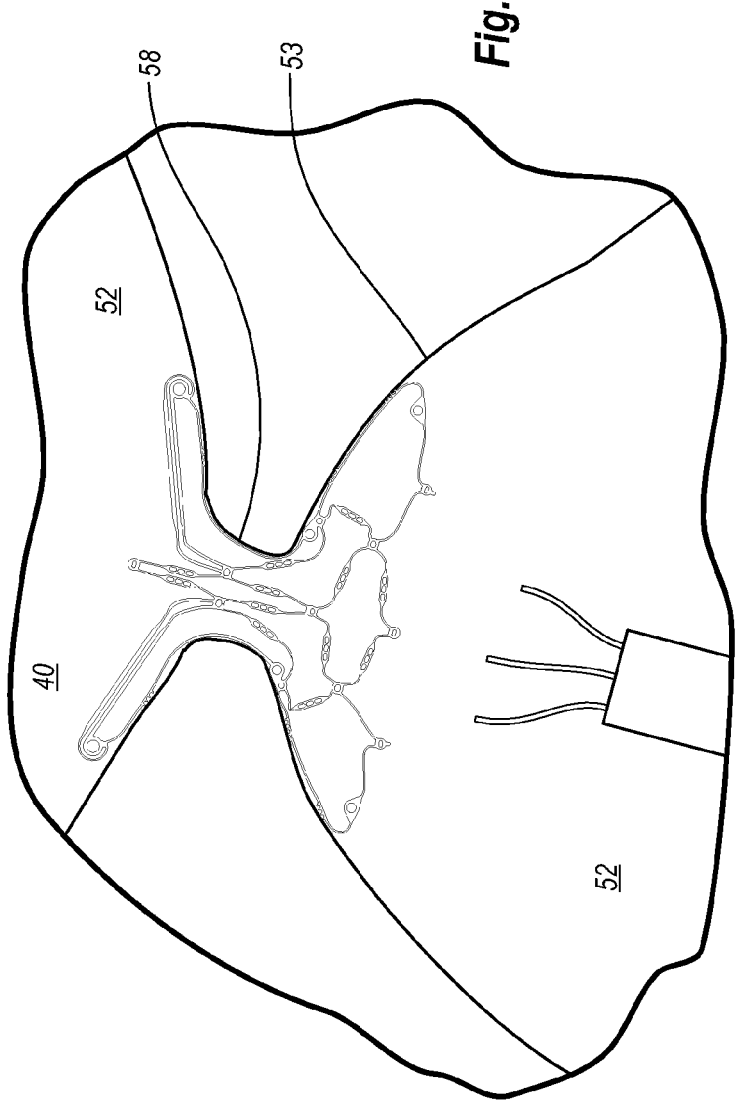
FIG. 10A illustrates an embodiment of a closure device positioned in an internal tissue opening.
Figure 10B:
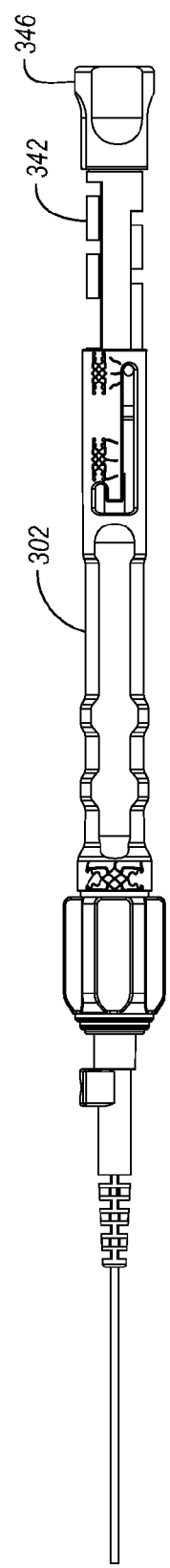
FIG. 10B illustrates an embodiment of a delivery device in an orientation corresponding to the deployed and detached closure device of FIG. 10A.

The biasing member 342 is configured to interact with the handle body 302 such that when the release pin 344 is positioned in a terminating portion of the release pin groove 310, as illustrated in FIG. 4, the biasing member 342 is biased in the proximal direction with respect to the handle body 302. In this manner, the release pin 344 can be moved from the terminating portion of the release pin groove 310, as illustrated in FIG. 4, to the opposing terminating portion of the release pin groove 310 adjacent the release indicia 308B by applying force to the biasing member 342 through the release knob 346 in the distal direction, rotating the release knob 346 and then moving the release knob 346 in the proximal direction to release the closure device 200, as illustrated in FIG. 10B.

FIG. 5A is a cross-sectional view of the distal end of the catheter 362. In the illustrated embodiment, the catheter 362 includes a delivery portion 366 for use in positioning the catheter 362. The catheter 362 can be made from a resilient material having sufficient axial stiffness to allow a practitioner to position the catheter 362 with respect to an internal tissue opening, and sufficient rotational stiffness to allow a practitioner to rotate the catheter 362 by rotating the handle body 302.

In one embodiment, the catheter 362 comprises a braided polyimide. In other embodiments, the catheter 362 can be made from a material having a sufficient axial stiffness, such as a braid reinforced polymer, axially reinforced polymer, metal reinforced polymer, carbon reinforced polymer, or some other type of axially stiff material. The delivery portion 366 can be made from a thermoplastic elastomer, such as PEBAX®. In other embodiments, the delivery portion or tip portion 366 can be made from a material having sufficient flexible properties, such as a polymeric material. In other embodiments, the delivery portion 366 can include a combination of materials, such as metallic materials and polymeric materials.

The delivery portion 366 can define a lumen 368 to facilitate placement of the catheter 362. For example, a guidewire can be received in the lumen 368 to guide the catheter 362 to a desired location. In this manner, the closure device 200 can be located proximate to the internal tissue opening in a quick and efficient manner. Furthermore, the delivery portion 366 can be shaped, such as including a bend, in order to facilitate placement of the delivery portion 366 through a PFO, for example. In one embodiment of the invention, the catheter 362 can be considered a rapid exchange catheter wherein the delivery or tip portion 366 enables a guidewire to be linked to the catheter 362 in a quick and efficient manner for placement of the catheter 362.

The catheter 362 and delivery portion 366 can be configured to at least partially house tethers 364 in a lumen which is distinct and separate from lumen 368. For example, lumen 368 can be in a spaced apart, non-coaxial arrangement from the lumen which houses tethers 364, such that a guidewire can be received through lumen 368 without being introduced into the lumen or space in which the tethers 364 are housed. In this manner, a user can introduce a guidewire into the lumen 368 at the distal end of the catheter 362, rather than the lumen which at least partially houses the tethers 364 which would require the guidewire to be introduced into the lumen at the proximal end of the catheter 362. In alternative embodiments, the lumen 368 configured to receive the guidewire therein can be positioned inside the lumen which houses the tethers 364. In this embodiment, lumen 368 would include an opening and an exit at the distal end of the catheter 362 in order to facilitate the quick placement of a guidewire through the lumen 368.

In one embodiment, catheter 362 can include a rounded cross-section and the delivery portion 366 can include a rectangular cross-section. The rectangular cross-section of the delivery portion 366 can facilitate proper deployment of the closure device 200 from the delivery device 300, as well as facilitate the closure device 200 being reintroduced back into the delivery portion 366. The rectangular cross-section of the delivery portion 366 can be sized to orient the tethers 364 next to each other in a linear fashion. In this manner, the likelihood that the tethers 364 cross each other upon reintroduction of the closure device 200 into the delivery portion 366 can be reduced.

In one embodiment of the invention, tethers 364 includes three tethers 364A-C, each tether 364 being sized and configured to attach to and/or accommodate therein an attachment member 240 of the closure device 200. One example of a tether is a line or hollow tube coupled to the handle body 302. The tether 364 can comprise a flexible, hollow shaft having sufficient stiffness such that as actuating assembly 320 moves the catheter 362 proximally with respect to the handle body 302, the closure device 200 is forced out of the delivery portion 366. Likewise, the tether 364 can be configured to pull the closure device 200 back into the delivery portion 366 as the actuating assembly 320 is moved distally with respect to the handle body 302.

Figure 7:
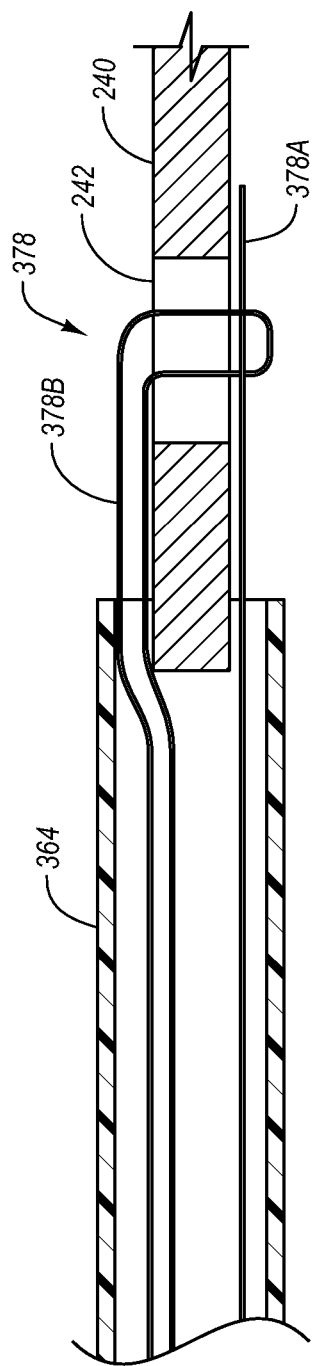
FIG. 7 illustrates an embodiment of a coupling system according to the present invention.

In one embodiment, the tether 364 can be a coil of stainless steel covered by a heatshrunk tubing to give the coil a degree of tensile strength and rigidity. In an alternative embodiment, the tether 364 can be a polymeric tube. In yet an additional embodiment, the tether 364 can be a combination of polymeric materials and metallic materials. In some embodiments, an additional heatshrunk tubing covers a proximal segment of the three tethers 364A-C. The heatshrunk covering can increase the column strength of the tether 364, which can enable the tethers 364 to assist with deployment and reintroduction of the closure device 200 from and into the delivery portion 366. The tethers 364 can have a distal tip configured to correspond to the shape and size of the attachment members 240 of the closure device, such that the attachment member 240 can be received into the distal tip of the tether 364, as illustrated in FIG. 7.

Tethers 364 can be made from a material having sufficient flexibility to substantially prevent distortion or otherwise influence the orientation of the closure device 200 when the closure device is deployed from the catheter 362, yet have sufficient axial strength to facilitate deployment of the closure device 200 when the catheter 362 is moved proximally with respect to the closure device 200. The tethers 364 can have a lumen extending therethrough of sufficient size and configuration to enable a plurality of wires 378 to be housed and movable therein.

Figure 5B:
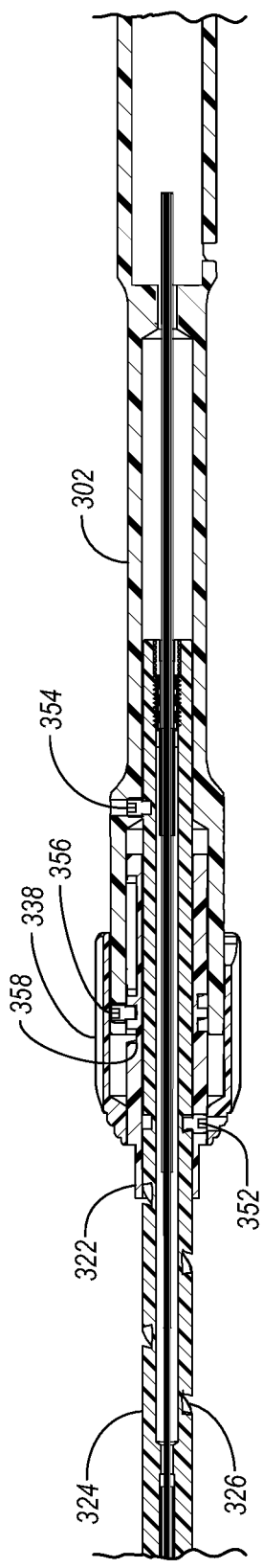
Figure 5C:
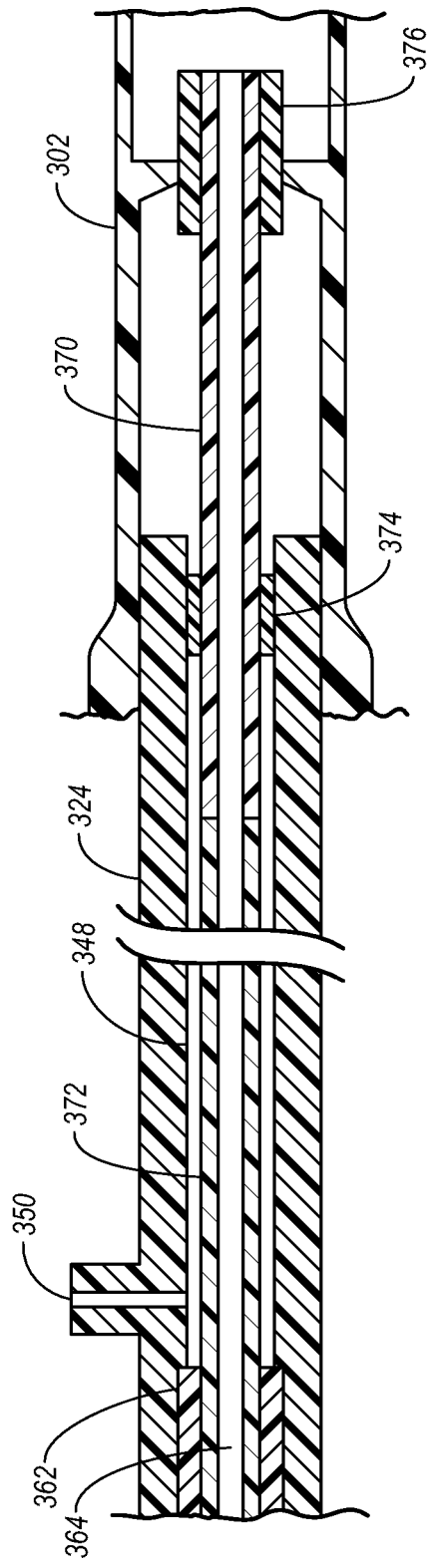

FIGS. 5B-5C are cross-sectional views illustrating the delivery assembly 360 in association with the actuating assembly 320. However, for simplicity, FIG. 5B does not include the biasing member 342 and associated release knob 346, and FIG. 5C illustrates details about the interaction between the delivery assembly 360 and the actuating assembly 320 without illustrating the first member 322 and details about the handle body 302 and the second member 324. In the illustrated embodiment, the proximal end of the catheter 362 is coupled to the distal end of the second member 324. In this manner, movement of the second member 324 can cause a corresponding movement in the catheter 362. For example, as the second member 324 moves proximally with respect to the handle body 302, so also does the catheter 362 move proximally with respect to the handle body 302.

According to one embodiment of the invention, the tethers 364 can extend from the delivery portion 366, through the catheter 362 and the second member 324 and are coupled to the handle body 302. The tethers 364 can be coupled to the handle body 302 by, for example, an intermediate member 376. The tethers 364 can be covered with a first and second housing 370, 372 to provide a degree of rigidity to the portions of the tethers 364 located inside of the handle body 302 and the second member 324. For example, in one embodiment, the first housing 370 comprises a rigid, hollow, metal rod configured to house the three tethers 364A-C therein. The first housing 370 can extend from the intermediate member 376, which facilitates securement of the tethers 364 to the handle body 302, and terminate at some point beyond the handle body 302.

In the illustrated embodiment, the second housing 372 can extend from the distal end of the first housing 370 and extend into the catheter 362. The second housing 372 can comprise a resilient material configured to resist axial stretching while allowing a degree of bending. In one embodiment, the second housing 372 comprises a coil of metal, such as stainless steel, configured to resist axial stretching, yet allow a degree of bending. The second housing 372 can allow a practitioner to bend a portion of the catheter 362, if needed, in order to manipulate delivery device 300 for placement of the closure device 200. A seal 374 can be provided between the first housing 372 and the second member 324 in order to reduce or substantially prevent bodily fluid, which may have entered the catheter 362, from entering the handle body 302 or otherwise inappropriately being expelled from the delivery device 300.

In the illustrated embodiment, the second member 324 can comprise an elongate shaft defining an axial lumen 348 and a lumen 350 in fluid communication therewith. Lumen 350 can be configured to couple to a medical device for removal of fluid from the delivery device 300. The axial lumen 348 can be sized to accommodate and allow movement of the tethers 362, the first housing 370 and the second housing 372 therein. The second member 324 can include a guide 326. The guide 326 can be configured to cooperate with a first pin 352 and a second pin 354 to influence movement of the second member 324 with respect to the handle body 302, as will be discussed more fully herein below.

In the illustrated embodiment, the first member 322 comprises a hollow elongate tube sized and configured to enable the second member 324 to be received into and moveable within the first member 322. The first member 322 can be operatively associated with the handle body 302 and the second member 324 to facilitate deployment of the closure device 200. For example, the first member 322 is linked to the handle body 302 by a third pin 356. The third pin 356 is received in a guide 358 of the first member 322. The guide 358 is configured to interact with the third pin 356 in order to influence the movement of the first member 322 with respect to the handle body 302.

The first pin 352 can link the first member 322 to the second member 324. When the first pin 352 links the first member 322 to the second member 324, the second pin 354 links the handle body 302 to the second member 324, and the third pin 356 links the handle body 302 to the second member 322, movement of the first member 322 can selectively deploy the closure device 200 from the delivery portion 366.

Figure 6:
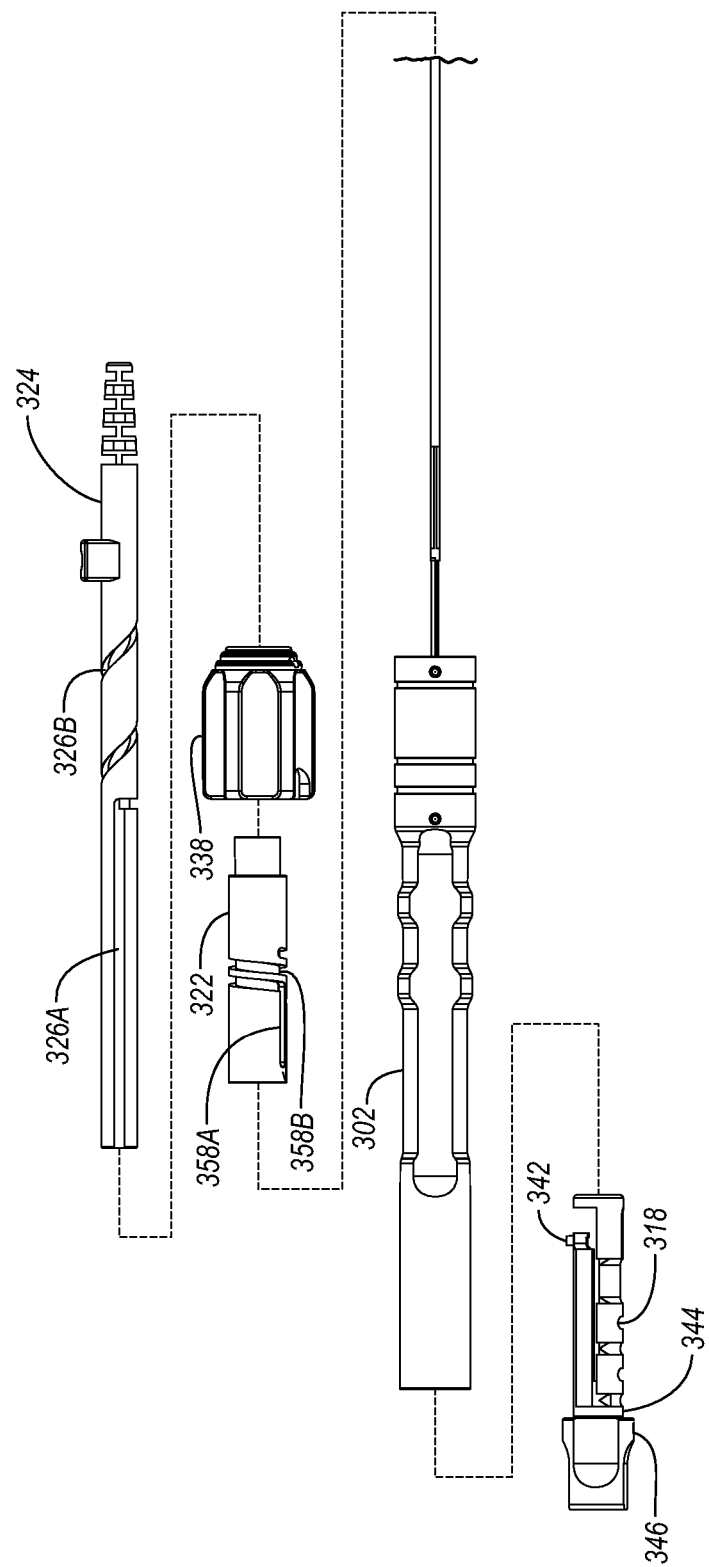
FIG. 6 illustrates an exploded view of a delivery device according to the present invention.

With reference to FIGS. 5A-C and 6, the association between the first member 322, the second member 324, the handle body 302 and the biasing member 342 will be discussed. FIG. 6 is an exploded view of the actuating assembly 320 and the release assembly 340. In the illustrated embodiment, the second member 324 is received into the first member 322, and the first member 322 is received into the knob 338 and the handle body 302, as illustrated in FIGS. 4 and 5B-5C.

According to one embodiment of the invention, the second member 324 can include a guide 326 having a first portion 326a and a second portion 326b, which guide 326 can be defined by a slot formed on the outer surface of the second member 324. In the illustrated embodiment, the first portion 326a is straight and extends along at least a portion of the length of the first member 324 and joins with the second portion 326b of the guide 326. The second portion 326b can include a helical groove or slot that begins with and is contiguous with the first portion 326a and extends distally therefrom.

The guide 326 of the second member 324 is configured to interact with the handle body 302 and the first member 322 to selectively retract the catheter 362 in order to deploy the closure device 200. For example, the first portion 326a of the guide 326 is configured to interact with the second pin 354, which is secured into the handle body 302 by means of threads and extend into the first portion 326a of the guide 326. In this manner, the second member 324 can move laterally with respect to the handle body 302. Thus, rotation of the handle body 302 can translate to rotation of the second member 324, and thus, the catheter 362 and the delivery portion 366.

The second portion 326b of the guide 326 is configured to interact with the first pin 352, which is secured to the first member 322 by means of threads and extends into the second portion 326b of the guide 326. In this manner, as the first member 322 is rotated, the first pin 352 will interact with the second portion 326b to move the second member 324 in the proximal direction. As the second member 324 is moved in the proximal direction with respect to the handle body 302, the catheter 362 moves proximally with respect to the handle body 302 thereby exposing or deploying the closure device 200 from the delivery portion 366.

In the illustrated embodiment, the first member 322 can include a guide 358 defined by a slot or groove formed in the outer surface of the first member 322. In the illustrated embodiment, the guide 358 can include a first portion 358a connected to a second portion 358b. The first portion 358a of guide 358 can be straight and extend along at least a portion of the length of the first member 322, and then join and be contiguous with the second portion 358b. The second portion 358b of the guide 358 can be a helical groove that wraps around at least a portion of the outer surface of the first member 322 and extends along at least a portion of the length of the first member 322.

As described previously, the third pin 356, which is secured to the handle body 302 by means of threads, can extend into the guide 358 in order to influence movement of the first member 322 with respect to the handle body 302. For example, as the third pin 356 is positioned in the most proximal portion of the first portion 358a, the closure device 200 is completely received into and enclosed by the delivery portion 366. As the first member 322 is moved in the proximal direction as illustrated by the arrow in FIG. 4, the third pin 356 moves in the first portion 358a of the guide 358 to deploy the first anchor 204 of the closure device 200 from the delivery portion 366.

The length of the first portion 358a can correspond with the distance that the first member 322, and thus the catheter 362, must move in order to deploy the first anchor 204 of the closure device 200 from the delivery portion 366. For example, a practitioner can move the knob 338, which is coupled to the first member 322, in the proximal direction. Movement of the knob 338 in the proximal direction can cause the third pin 356 to move linearly in the first portion 358a of the guide 358. In this manner, the second member 324 can move correspondingly with the first member 322 because of the first pin 352, which links the first member 322 to the second member 324. As the third pin 356 is positioned in the location of the guide 358 where the first portion 358a meets with the second portion 358b, the first member 322 can be rotated in order to selectively deploy the remaining portions of the closure device 200 from the delivery portion 366 of the delivery device 300.

As the first member 322 is rotated, the third pin 356 is positioned in the second portion 358b to influence movement of the first member 322 with respect to the handle body 302, and the first pin 352, which is coupled to the first member 322, interacts with the second portion 326b of the guide 326 to move the second member 324 in the proximal direction with respect to the handle body 302. Movement of the second member 324 in the proximal direction in this manner can cause further deployment of the closure device 200 from the delivery portion 366. As will be appreciated, the knob 338 can be coupled to the first member 322 to facilitate and enable movement of the first member 322 with respect to the handle body 302.

The dual movement required to deploy the closure device 200 can provide some efficiency and safety advantages. For example, a practitioner can move the knob 338 in a first direction (i.e., proximally in a linear fashion) to deploy the first anchor 204 from the delivery portion 366. Thereafter, the practitioner can move the handle body 302 to position the first anchor 204 against the wall tissue of an internal tissue opening, such as against the left atrial wall of a heart, for example. Once the first anchor 204 is positioned against the wall, the practitioner can move the knob 338 in a second direction (i.e., rotate the knob) to further deploy the closure device 200 from the delivery portion 366. The dual movement enables a user to predict the deployment of the closure device 200 to reduce the risk of premature deployment of the closure device.

It will be understood by one of ordinary skill in the art in view of the disclosure provided herein that other means of controlling movement of one member with respect to the other, such as the first member with respect to the second member, can be utilized without departing from the scope and spirit of the invention. For example, a structure configured to substantially restrict or control movement of the first element with respect to the second element and/or handle body can be utilized. In one embodiment, the structure can include a cam and a follower. In an alternative embodiment, the structure can include a slider.

The release assembly 340 can be configured to be received in the proximal end of the handle body 302. The release assembly 340 can be configured to provide additional safety features for the practitioner and patient by reducing the risk of premature detachment of the closure device 200 before it is positioned appropriately in an internal tissue opening. For example, a practitioner using the medical system 100 of the present invention can manipulate the actuating assembly 320 to deploy the closure device 200 for positioning in an internal tissue opening. In order to deploy a first portion of the closure device 200, a user can move the knob 338, and thus the first member 322, in the proximal direction with a first movement, which is a linear movement, then deploy the remaining portions of the closure device 200 by a rotational movement. Once the closure device 200 is deployed, the practitioner can be required to move their hands in order to utilize the release assembly 340 to release the closure device 200 from the delivery device 300.

In the illustrated embodiment the release assembly 340 can include a release knob 346 coupled to a biasing member 342, which is received into the proximal end of the handle body 302. The biasing member 342 can be configured to include a plurality of slots 318 configured and arranged to act similar to a spring. The slots 318 can be configured and arranged in the biasing member 342 to enable at least a portion of the biasing member 342 to be compressed. Compression of the biasing member 342 can cause the release pin 344 to move toward the distal end of the biasing member 342.

The biasing member 342 can be configured such that when biasing member 342 is positioned in the handle body 302, the biasing member 342 naturally tends to maintain its position with the release pin 344 in the release pin groove 310 as illustrated in FIG. 4. As force is applied to the release knob 346 in the distal direction (i.e., compress the biasing member 342), the release pin 344 can be moved out of a terminating portion of the release pin groove 310 and rotated and moved into a proximal terminating portion of the release pin groove 310 to release the closure device 200 from the delivery device 300.

The closure device 200 is released from the delivery device 300 by moving a plurality of wires 378 which are housed by a tether 364 and coupled to the biasing member 342. Illustrated in FIG. 7 is a cross-sectional view of attachment member 240 of the closure device 200 received into a tether 364 and coupled by first and second wires 378a, 378b. In the illustrated embodiment, a second wire 378b can extend through and out of the tether 364 and form a loop. The loop can extend through an aperture 242 of the attachment member 240 of the closure device 200. With the loop of second wire 378b positioned through the aperture 242 of the attachment member 240, a first wire 378a, which extends through and out of the tether 364, can extend through the loop of the second wire 378b to form a locking feature. When the first wire 378a extends sufficiently through the loop of the second wire 378b, the closure device 200 can remain coupled to the delivery device 300 until the first wire 378a is pulled through the loop of the second wire 378b, and the second wire 378b is pulled out of the aperture 242 of the attachment member 240.

The first wire 378a and the second wire 378b can be attached at their proximal ends to the biasing member 342. In this manner, movement of the biasing member 342 in the proximal direction can cause movement of the wires 378 also in the proximal direction. In one embodiment, the wires 378 can be coupled to the biasing member 342 such that movement of the biasing member 342 will cause the first wire 378a to move a distance sufficient to be removed from the loop of second wire 378b before the second wire 378b is moved by the biasing member 342. The wire 378 can comprise a metallic wire, such as a NiTiNol wire. The wire 378 can also include a stainless steel wire or some other type of metal or stiff polymer. The wires 378 can be made from a material having a sufficient tensile strength to secure the closure device 200 to the tethers 364 without causing the wires 378 to fail or substantially deform. In one embodiment of the invention, the wire 378B can include a stainless steal wire and wire 378A can include a NiTiNol wire.

Other types and configurations of biasing members can be utilized without departing from the scope and spirit of the invention. For example, in one embodiment, the release assembly can include a rotating member coupled to the securing elements. In this embodiment, rotation of the rotating member can cause the securing elements to wind around the rotating member thereby causing the distal ends of the securing elements to move proximally with respect to the handle body.

Figure 8A:
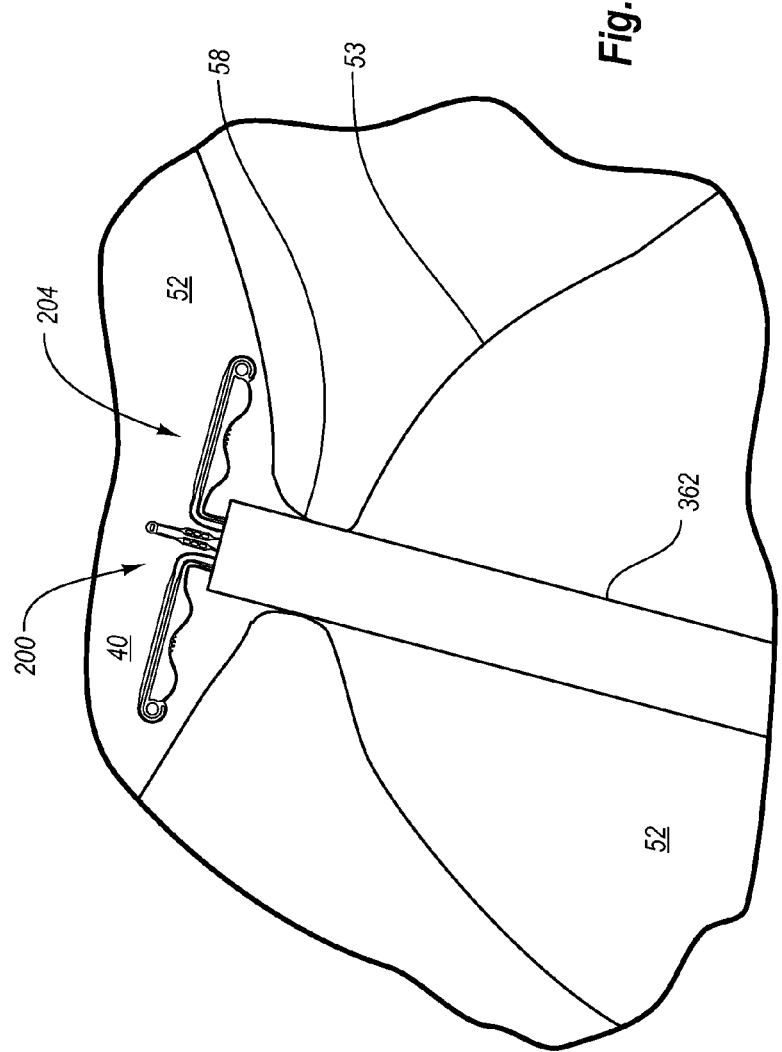
FIG. 8A illustrates an embodiment of a closure device being partially deployed in an internal tissue opening.
Figure 8B:
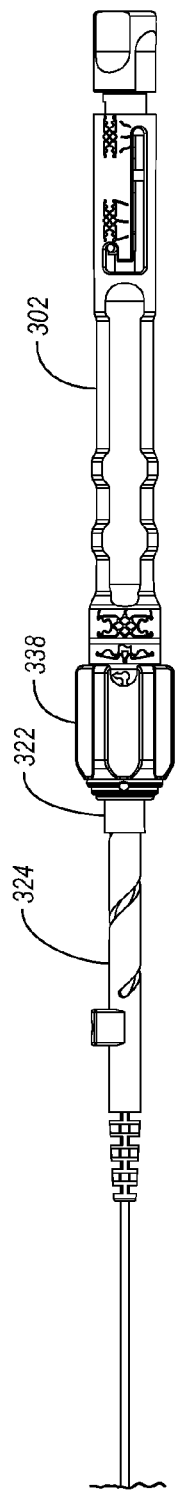
FIG. 8B illustrates an embodiment of a delivery device in an orientation corresponding to the partially deployed closure device of FIG. 8A.
Figure 9:
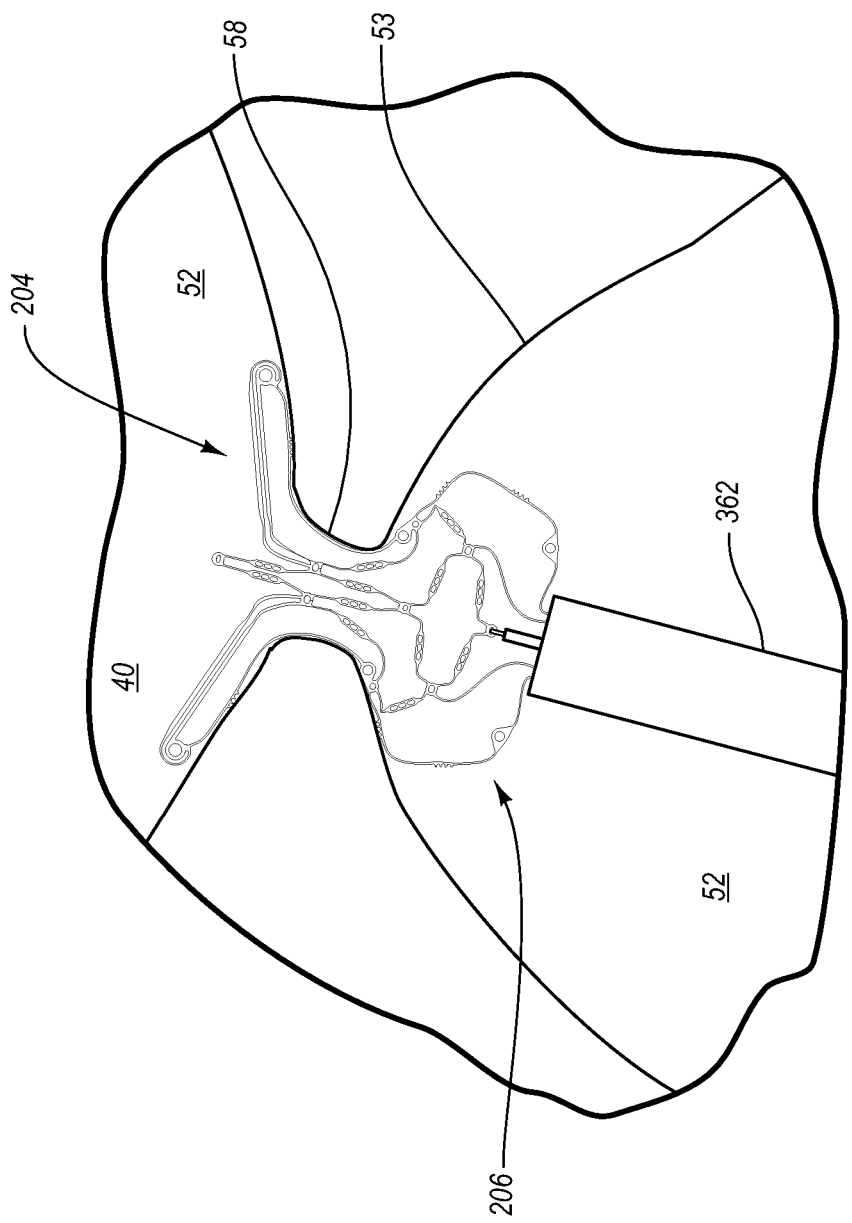
FIG. 9 illustrates an embodiment of a partially deployed closure device according to the present invention.

The method of use of the medical system 100 will now be described with reference to a particular internal tissue opening, namely a PFO. FIG. 8a illustrates the positioning of the catheter 362 through the tunnel 58 of a PFO with the first anchor 204 of the closure device 200 deployed. The medical system 100 is utilized to close an internal tissue opening by positioning the catheter 362 through an internal tissue opening and moving the first member 322 by a first movement (i.e., linearly) in the proximal direction to deploy the first anchor 204 of the closure device 200. After the first anchor 204 of the closure device 200 is deployed, the delivery device 300 can be moved in the proximal direction in order to seat the first anchor 204 against the wall of the tissue opening or otherwise engage the wall of the internal tissue opening, as illustrated in FIG. 9. This can be done by moving the handle body 302 in the proximal direction.

After the first anchor 204 has been positioned against the wall of the internal tissue opening, the knob 338, and thus the first member 322, can moved by a second movement, or in other words, rotated to deploy additional portions of the closure device 200 as illustrated in FIG. 9. After the closure device 200 has been fully deployed and conforms to the anatomy of the internal tissue opening, the release assembly 340 can be actuated to selectively detach the delivery device 300 from the closure device 200 as illustrated in FIGS. 10a and 10b.

The release assembly 340 can be actuated by moving the biasing member 342 distally with respect to the handle body 302, then rotating the biasing member with respect to the handle body 302, and then moved proximally with respect to the handle body 302. In this manner, closure device 200 substantially conforms to the anatomy of the internal tissue opening. As noted previously, the configuration of the closure device 200 is such that when positioned in the internal tissue opening as illustrated, the members of the closure device 200 apply lateral force to the tissue of the internal tissue opening, such as the tunnel 58 of the PFO, to approximate tissue of the PFO for closure.

Figure 11A:
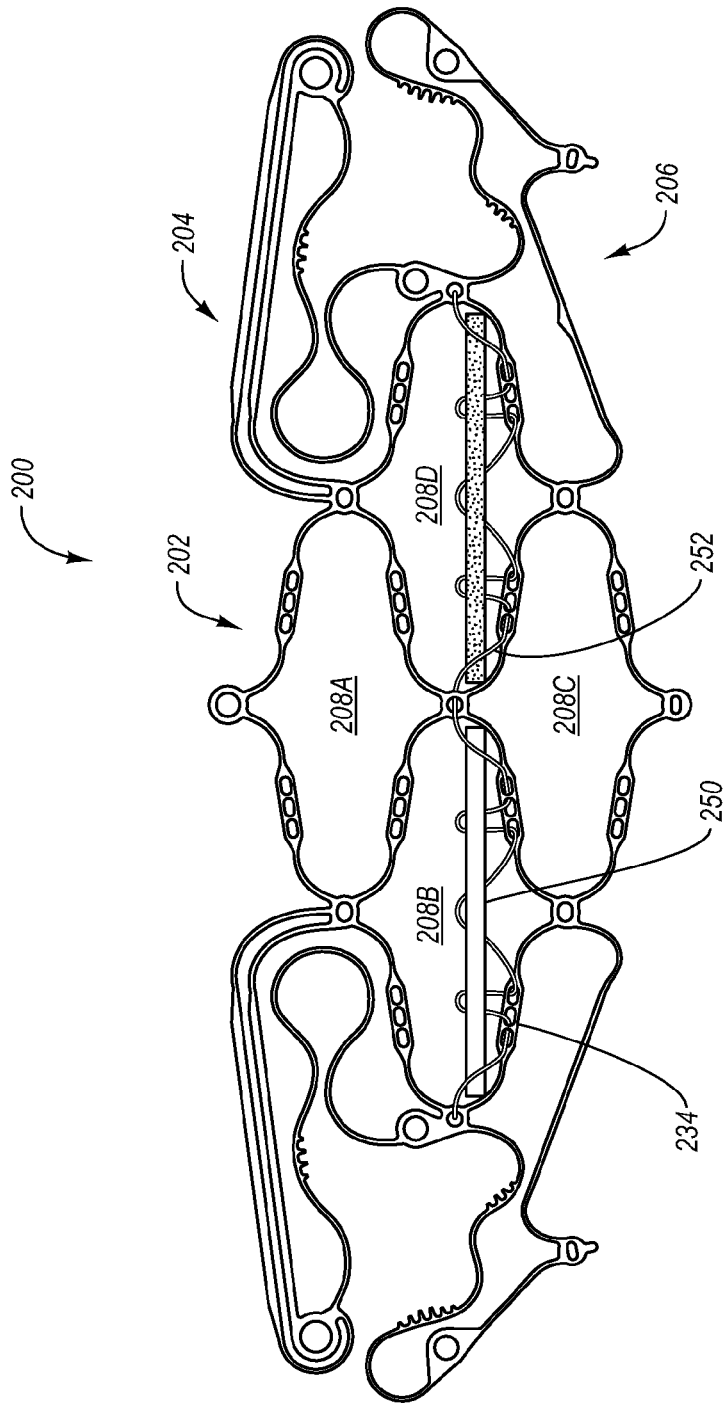
FIG. 11A illustrates an embodiment of a closure device having an ingrowth material according to the present invention.

FIG. 11A illustrates one embodiment of a closure device 200 that can include a member 250, such as an ingrowth material. The member 250 can be configured to induce tissue growth. The member 250 can be fixed to the closure device 200 by means of a securing element, such as a thread 252. For example, the thread 252 can extend through the member 250 and through the apertures in the intermediate portions 234 in order to secure the member 250 to the closure device 200. In other embodiments, the member 250 can be secured to the closure device 220 by a known securing means, such as by an adhesive, a heat weld, or some other known or hereafter developed means for securement.

The member 250 and the thread 252 can include a bio-resorbable material, such as polylactide or polyglycolide or collagen. The member 250 can be sized and configured to enable the closure device 200 to be deployed from and received into the delivery portion 366 of the delivery device 300. Furthermore, the member 250 can be configured to interact with tissue of the internal tissue opening to stimulate growth of tissue for closure of the internal tissue opening. For example, the member 250 can interact with the tunnel tissue 58 of a PFO in order to stimulate growth of tissue in the PFO tunnel 58.

The member 250 can be any suitable material which can or tends to promote tissue growth. Examples of such material can include a polymeric material, or a woven material, such as a woven metallic or biological material. In one embodiment, the member 250 can be a piece of foam. In alternative embodiments, the member 250 can be a piece of yarn, fabric or string, or some combination thereof. Other tissue growth promoting members can include a coating disposed on the closure device 200. In other embodiments, the member 250 can be a piece of foam, braided material such as a piece of yarn or string, or fabric which has a coating disposed thereon.

The member 250 can include materials such as a piece of polyurethane or some other biocompatible polymer, including bio-resorbable polymers. The member 250 can also include Dacron or polymeric threaded material which have been woven or knitted, or formed into compressed, non-woven fabrics. The member 250 can also include a metallic material, such as a NiTiNol, stainless steal or some other biocompatible alloy or bio-resorbable metal, such as magnesium alloy, or some combination thereof. In one embodiment, the member 250 comprises a metallic wire.

FIG. 11B illustrates a side view of the closure device 200, and illustrates one example of the closure device having a substantially flat configuration. In the illustrated embodiment, the closure device 200 can include a depth or depth thickness designated as DT, and a plane 260 extending perpendicular into and out of the plane of the page. In this embodiment, the member 250 can extend beyond at least a first edge 262 of the closure device 200. Furthermore, the member 250 can extend beyond both the first edge 262 and a second edge 264 of the closure device 200. In this manner, member 250 can contact tissue adjacent the closure device 200 to promote tissue growth in the tissue opening.

The member 250 can be sized and configured to extend beyond at least the first edge 262 of the closure device 200 a sufficient distance to contact tissue of the tissue opening. In one embodiment, the member 250 can extend beyond at least the first edge 262 a sufficient distance to contact tissue adjacent the first edge 262, thereby causing the end of the member 250 which is in contact with the tissue to deflect or bend. In this manner, more surface area of the member 250 can be in contact with tissue to thereby facilitate an increase in tissue growth. In other embodiments, the member 250 can extend beyond both the first edge 262 and the second edge 264 a sufficient distance to cause both ends of the member 250 to bend, which can result in more surface area contacting the tissue. In one embodiment, the member 250 can extend between at least 0.5 mm and 5 mm beyond the first edge 262. In another embodiment, the member 250 can extend between at least 0.5 mm and 5 mm beyond the first edge 262, and can extend between at least 0.5 mm and 5 mm beyond the second edge 264. Furthermore, the member 250 can have a thickness of between at least 0.25 mm and 2 mm.

In addition, in some embodiments the member 250 can be configured to decrease the size of a remaining void in the tissue opening after the closure device 200 has been positioned in the tissue opening. Member 250 extending beyond the first edge 262 of the closure device 200 is an example of the member 250 extending substantially out of plane of the substantially flat configuration.

The present invention can also include the following methods, systems and devices.

A medical device comprising: a body portion comprising two or more cells, said body portion being movable between a deployed and non-deployed orientation; and at least one anchor linked to said body portion, said at least one anchor being adapted to reduce proximal movement of the medical device when the medical device is positioned in an internal tissue opening.

A medical device comprising: a multi-cellular structure adapted to selectively expand and contract between a deployed and non-deployed orientation; a first anchor operatively associated with said multi-cellular structure, said first anchor being adapted to selectively engage at least a portion of a wall of an internal tissue opening; and a second anchor operatively associated with said multi-cellular structure, said second anchor being adapted to engage at least a portion of at least another portion of the wall of the tissue opening.

A method for closing a Patent Foramen Ovale, comprising the steps of: positioning at least a portion of a medical device into a left atrium of a heart, said medical device comprising a first anchor, a multi-cellular structure linked to said first anchor, and a second anchor linked to said multi-cellular structure, said first anchor, said multi-cellular structure and said second anchor being adapted to selectively move between a non-deployed and deployed orientation; locating at least a portion of said first anchor against at least a portion of a left atrial wall of the heart; and locating at least a portion of said second anchor against at least a portion of at least one of a tunnel of the Patent Foramen Ovale or a right atrial wall of the heart.

A medical device for approximating tissue of an internal tissue opening together, the medical device comprising: a body portion comprising two or more cells, said body portion being adapted to apply lateral force to tissue of an internal tissue opening; and at least one anchor operatively associated with said body portion.

A medical device for approximating tissue of an internal tissue opening together, the medical device comprising: a multi-cellular structure adapted to selectively expand and contract between a deployed and non-deployed orientation, said multi-cellular structure configured to preferentially expand; and at least one anchor operatively associated with said multi-cellular structure, said at least one anchor being adapted to move between a deployed and non-deployed orientation, at least a portion of said at least one anchor being adapted to apply lateral force to at least a portion of tissue of an internal tissue opening when said first anchor is deployed.

A method for reducing the size of an internal tissue opening, comprising the steps of: positioning at least a portion of a medical device through an internal tissue opening, said medical device comprising a multi-cellular structure and at least a first anchor associated with said multi-cellular structure, said at least one anchor and said multi-cellular structure being adapted to selectively move between a non-deployed and deployed orientation; and applying lateral force to tissue of the internal tissue opening by at least partially deploying said at least one anchor.

A medical device comprising: two or more cells forming a body portion, said body portion being adapted to move between a collapsed and expanded orientation to apply lateral force to tissue of an internal tissue opening; and at least one anchor linked to said body portion, said at least one anchor being adapted to extend distally when said at least one anchor is collapsed and extend laterally when said at least one anchor is moved from a collapsed to an expanded orientation.

A method for deploying a closure device, the method comprising the steps of deploying a left anchor of a closure device from a delivery device, said delivery device comprising an actuating assembly operatively associated with a handle body, said left anchor being adapted to deploy by linearly moving at least a portion of said actuating assembly with respect to said handle body; and deploying a second anchor of said closure device from said delivery device by rotating at least a portion of said actuating assembly with respect to said handle body.

A delivery device for an internal tissue opening closure device, the delivery device comprising: a handle body including first and second guide members; a first member operatively associated with said handle body, at least a portion of said first member defining a guide, said first guide member cooperating with said guide to influence movement of said first member with respect to said handle body, said first member including a guide structure; and a second member operatively associated with said first member, at least a portion of said second member defining a second guide, said guide structure cooperating with said second guide to influence the movement of said second member with respect to said first member, and said second guide member cooperating with said second guide to influence the movement of said second member with respect to said handle body.

A delivery device for an internal tissue opening closure device, the delivery device comprising: a handle body; a first pin coupled to said handle body; a second pin coupled to said handle body; a first cam adapted to be at least partially received into and movable with respect to at least a portion of said handle body, said first cam including a slot formed on an external surface of said first cam, said slot including a first portion and a second portion, said first portion of said slot extending along at least a portion of the length of said first cam, said second portion of said slot extending at least partially around said first cam, said first pin received in said slot; a third pin coupled to said first cam; and a second cam adapted to be at least partially received into and movable with respect to at least a portion of said first cam, said second cam including a first and second slot formed on an external surface of said second cam, said first slot of said second cam extending at least partially around said second cam and said second slot of said second cam extending along at least a portion of the length of said second cam, said third pin received in said first slot of said second cam and said second pin received in said second slot of said second cam.

A medical device for closing an internal tissue opening, the medical device comprising: a multi-cellular structure configured to assume a substantially flat configuration; at least one anchor operatively associated with said multi-cellular structure, said at least one anchor comprising a plurality of segments at least partially defining a closed periphery.

A medical device for closing an internal tissue opening, the medical device comprising: a multi-cellular structure adapted to be moveable between a first orientation and a second orientation; at least one anchor operably associated with said multi-cellular structure; and a tissue growth member associated with said multi-cellular structure, said tissue growth member being adapted to enhance tissue growth in the internal tissue opening.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A delivery device for delivering a medical device from a catheter, the delivery device comprising:
   a handle body defining a longitudinal axis extending therethrough; and
   an actuating assembly operatively associated with said handle body and configured to unsheathe the medical device from the catheter, said actuating assembly including a linear guide defining a linear slot extending parallel to the longitudinal axis and a helical guide defining a helical slot, said actuating assembly being adapted to move linearly with respect to said handle body to an end of the linear slot to unsheathe at least a first portion of the medical device from the catheter, and, once fully moved linearly along the linear guide, to then rotate with respect to said handle body along the helical slot of the helical guide to unsheathe at least a second portion of the medical device from the catheter; wherein said actuating assembly comprises a first member adapted to move linearly with respect to said handle body to unsheathe said at least a first portion of the medical device; wherein said actuating assembly comprises a second tubular member adapted to rotate with respect to said handle body to unsheathe said at least a second portion of the medical device, the first member slidably positioned relative to and movable within said second tubular member such that the second tubular member is rotatable relative to the first member; and wherein the linear slot is contiguous with the helical slot.

2. A delivery device as recited in claim 1, further comprising a release assembly adapted to facilitate detachment of the medical device from the delivery device.

3. A delivery device as recited in claim 1, further comprising a delivery assembly adapted to facilitate delivery of the medical device.

4. A delivery device as recited in claim 1, further comprising a catheter linked to said actuating assembly, wherein said catheter comprises a first lumen and second lumen in a non-coaxial arrangement.

5. A delivery device for delivering a Patent Foramen Ovale closure device, the delivery device comprising:
   a handle body defining a longitudinal axis extending therethrough;
   a catheter having a proximal end and a distal end, the proximal end coupled to said handle body and the distal end configured to contain the closure device;
   a first member operatively associated with said handle body, said first member including a linear guide defining a linear slot therein extending linearly parallel to the longitudinal axis and being adapted to move linearly along the linear slot with respect to said handle body to partially unsheathe the closure device from the distal end of the catheter; and
   a second tubular member including a helical guide defining a helical slot therein, said second tubular member being linked to said handle body and said first member, said second tubular member, upon the first member being fully moved to partially unsheathe the closure device, being adapted to move linearly with respect to said handle body and adapted to rotate along said helical slot with respect to said handle body and said first member to fully unsheathe the closure device from the distal end of the catheter, said first member slidably positioned relative to and moveable within said second tubular member such that the second tubular member is rotatable relative to the first member.

6. A delivery device as recited in claim 5, wherein said first member is linked to said handle body by a pin.

7. A delivery device as recited in claim 5, wherein linear movement of said first member with respect to said handle body causes at least a first portion of the closure device to be unsheathed.

8. A delivery device as recited in claim 5, wherein said first member is configured to linearly move with respect to said handle body and is configured to unsheathe a first anchor of the closure device.

9. A delivery device as recited in claim 5, wherein said second tubular member is configured to rotationally move with respect to said handle body and is configured to unsheathe a second anchor of the closure device.

10. A delivery device as recited in claim 5, wherein said catheter comprises tether lines extending through a catheter lumen such that said tether lines are sized and configured to extend between and are coupled to said handle body and the closure device.

11. A medical system for treating an internal tissue opening, the system comprising:
   a medical device; and
   a delivery device comprising:
      a handle body defining a longitudinal axis extending therethrough;
      a catheter having a proximal end and a distal end, the proximal end coupled to said handle body and the distal end configured to contain the medical device; and
      an actuating assembly operatively associated with said handle body, said actuating assembly being adapted to selectively unsheathe a first portion of said medical device from the distal end of the catheter by a first mechanism, the first mechanism including a linear guide defining a linear slot and extending parallel with the longitudinal axis and configured to actuate by linear movement of a knob along the linear slot, and said actuating assembly being adapted to selectively unsheathe a second portion of said medical device from the distal end of the catheter by a second mechanism, the second mechanism including a helical guide defining a helical slot and, upon full linear movement of the knob, configured to actuate by rotational movement of the knob along the helical slot, the first mechanism and the second mechanism configured to be sequentially actuated to distinguish which of the first portion and the second portion of the medical device is being unsheathed from the catheter; wherein said first mechanism comprises a first member adapted to move linearly with respect to said handle body to unsheathe the first portion of the medical device; and wherein said second mechanism comprises a second tubular member adapted to rotate with respect to said handle body to unsheathe the second portion of the medical device, the first member slidably positioned relative to and moveable within said second tubular member such that the second tubular member is rotatable relative to the first member.

12. A medical system as recited in claim 11, wherein said medical device comprises a multi-cellular structure and at least one anchor operatively associated with said multi-cellular structure.

13. A medical system as recited in claim 11, wherein said first mechanism comprises a linear movement of the knob.

14. A medical system as recited in claim 11, wherein said second mechanism comprises a rotational movement of the knob.

15. A medical system as recited in claim 11, wherein said medical device comprises a substantially flat frame.

* * * * *